United States Patent [19]
Nietupski et al.

[11] Patent Number: 5,147,778
[45] Date of Patent: Sep. 15, 1992

[54] PROBES AND METHODS FOR THE DETECTION OF SALMONELLA

[75] Inventors: Raymond M. Nietupski, Millbury; Stephen G. Wilson, Southbridge, both of Mass.; Jyotsna Shah, Nashua, N.H.; Samuel W. Chan, Newton, Mass.; Donald N. Halbert; David J. Lane, both of Milford, Mass.

[73] Assignee: Amoco Corporation, Chicago, Ill.

[21] Appl. No.: 277,579

[22] Filed: Nov. 29, 1988

Related U.S. Application Data

[63] Continuation-in-part of Ser. No. 127,484, Dec. 1, 1987, abandoned.

[51] Int. Cl.$^5$ .............. C12Q 1/68; C12Q 1/02; C07H 15/12; G01N 33/48
[52] U.S. Cl. .......................... 435/6; 435/29; 435/879; 536/26; 536/27; 536/28; 536/29; 436/501; 436/94; 935/77; 935/78
[58] Field of Search .............. 435/6, 810, 879; 436/501, 94; 536/28, 27; 935/77, 78

[56] References Cited

U.S. PATENT DOCUMENTS

| 4,689,295 | 8/1987 | Taber et al. | 536/27 |
| 4,717,653 | 1/1988 | Webster, Jr. | 435/6 |
| 4,816,389 | 3/1989 | Sansonetti et al. | 436/501 |
| 4,851,331 | 7/1989 | Vary et al. | 935/77 |

FOREIGN PATENT DOCUMENTS 8803957 6/1988 World Int. Prop. O. ............. 435/6

Primary Examiner—Margaret Moskowitz
Assistant Examiner—Stephanie W. Zitomer
Attorney, Agent, or Firm—Norval B. Galloway; William H. Magidson; Robert J. Wagner

[57] ABSTRACT

Improved nucleic acid probes capable of specifically hybridizing to rRNA of Salmonella and not to rRNA of non-Salmonella are described along with methods utilizing such probes for the detection of Salmonella in food and other samples.

8 Claims, 1 Drawing Sheet

5,147,778

PROBES AND METHODS FOR THE DETECTION OF SALMONELLA

The present application is a continuation-in-part of a co-pending application entitled "Detection of Salmonella," U.S. Ser. No. 127,484, filed Dec. 1, 1987, now abandoned.

FIELD OF THE INVENTION

This invention relates to detecting bacteria belonging to the genus Salmonella and more specifically provides nucleic acid probes and compositions along with methods for their use for the specific detection of Salmonella.

BACKGROUND OF THE INVENTION

The term "Salmonella" as used herein, refers to the bacteria classified as such in Bergey's Manual of Systematic Bacteriology (N. R. Krieg [ed.], 1984, 427–458, Williams & Wilkins). Detection of Salmonella is important in various medical and public health contexts. The Salmonella species are important agents of human disease. Salmonella bacteria can cause a variety of pathological conditions ranging from simple gastroenteritis to more severe illnesses.

It is, therefore, an aspect of the present invention to provide a novel assay system capable of rapidly detecting Salmonella and which is generally applicable to environmental, food or clinical samples.

Pursuant to a standard laboratory method and a method recommended by the F.D.A. (FDA/BAM Bacteriological Analytical Manual, Chapter 7, 6th Edition, 1984, Supplement 9/87', Association of Official Analytical Chemists), the presence of Salmonella in environmental or food specimens has been traditionally detected by culturing an appropriately prepared sample on microbiological media under conditions favorable for growth of these organisms. The resulting colonies are then typically examined for morphological and biochemical characteristics, a process that generally is initiated 48 hours after acquisition of the sample and disadvantageously takes several days to complete.

It is another aspect of the present invention to avoid the disadvantage associated with traditional culturing techniques by providing more rapid methods to detect Salmonella.

Taber et al., U.S. Pat. No. 4,689,295, disclose the use of DNA probes specific for Salmonella DNA to detect the presence of bacteria of the genus Salmonella in food. There is generally, however, only one DNA copy per organism and thus a limited number of detectable "targets".

It is still yet another aspect of the present invention to provide probes and methods not limited to detecting DNA.

Ribosomes are of profound importance to all organisms because they serve as the only known means of translating genetic information into cellular proteins, the main structural and catalytic elements of life. A clear manifestation of this importance is the observation that all cells have ribosomes.

Ribosomes contain three distinct RNA molecules which, at least in *E. coli*, are referred to as 5S, 16S, and 23S rRNAs. These names historically are related to the size of the RNA molecules, as determined by sedimentation rate. In actuality, however, they vary substantially in size between organisms. Nonetheless, 5S, 16S, and 23S rRNA are commonly used as generic names for the homologous RNA molecules in any bacteria, and this convention will be continued herein.

Kohne et al. (1968) Biophysical Journal 8:1104–1118 discuss one method for preparing probes to rRNA sequences.

Pace and Campbell, Journal of Bacteriology 107:543–547 (1971), discuss the homology of ribosomal ribonucleic acids from diverse bacterial species and a hybridization method for quantitating such homology levels. Similarly, Sogin et al., Journal of Molecular Evolution 1:173–184 (1972), discuss the theoretical and practical aspects of using primary structural characterization of different ribosomal RNA molecules for evaluating phylogenetic relationships.

Fox et al., International Journal of Systematic Bacteriology (1977), discuss the comparative cataloging of 16S ribosomal RNAs as an approach to prokaryotic systematics. Hogan et al., International Patent Application publication number WO88/03957, disclose a number of oligonucleotides that hybridize to some Salmonella rRNAs. None of these references, however, by themselves or in combination teach or predict the improved probes or methods of the present invention.

Lane, Rashtchian, and Parodos in copending U.S. Ser. No. 127,484 discloses a number of oligonucleotide probes for Salmonella rRNA and assay formats which enhance their utility. While the probes described therein work well, it is yet still another aspect of the present invention to provide further improved Salmonella-specific, rRNA targeted probes and probe sets and strategies for maximizing their utility.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially) to target nucleic acid sequences.

Hybridization is traditionally understood as the process by which, under predetermined reaction conditions, two partially or completely complementary single-stranded nucleic acids are allowed to come together in an antiparallel fashion to form a double-stranded nucleic acid with specific and stable hydrogen bonds. The stringency of a particular set of hybridization conditions is defined by the base composition of the probe/target duplex, as well as by the level and geometry of mispairing between the two nucleic acids. Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will largely dictate the preferred probes to be employed. Such relationships are well understood and can be readily manipulated by those skilled in the art. As a general matter dependent upon probe length, such persons understand stringent conditions to mean approximately 35° C.–65° C. in a salt solution of approximately 0.9 molar sodium chloride. A target nucleic acid sequence is one to which a particular probe is capable of preferentially hybridizing.

SUMMARY OF THE INVENTION

In accordance with the various principles and aspects of the present invention, there are provided nucleic acid probes and probe sets comprising DNA or RNA sequences which, under specific hybridization conditions, are capable of detecting the presence of ribosomal RNA (rRNA) molecules of most or all Salmonella or the DNA encoding such rRNA (rDNA) but which are not capable, under the same conditions, of detecting the rRNA or rDNA of other related bacteria which may be present in the test sample.

The present invention also features an assay system or kit for the utilization of these probes, the format of which can enhance the aforementioned desirable behavior of the probes. The most preferred assay system of the present invention advantageously exhibits one or more of the following enhanced performance capabilities with respect to other currently available means for detection of Salmonella:

a) increased sensitivity; i.e., the ability to detect fewer Salmonella in a given sample than currently available methods;

b) potentially significant reductions in assay cost due to the use of inexpensive reagents and reduced labor;

c) accurate identification of even biochemically unusual Salmonella, even when biochemically closely related genera are present, because of the rRNA sequence characterizations which provide the basis of such identification;

d) rapid results because the test is performed on mixed cultures of organisms; Salmonella need not be isolated from the test sample. Accordingly, the preferred test of this invention advantageously takes only two days to provide a result; and e) greater convenience because the assay lends itself to non-isotopic detection of Salmonella.

It has been discovered that other advantages incurred by directing the probes of the present invention against rRNA include the fact that the rRNAs detected constitute a significant component of cellular mass. Although estimates of cellular ribosome content vary, actively growing Salmonella bacteria may contain upwards of $5.0 \times 10^4$ ribosomes per cell, and therefore $5.0 \times 10^4$ copies of each of the rRNAs (present in a 1:1:1 stoichiometry in ribosomes). In contrast, other potential cellular target molecules such as genes or RNA transcripts thereof, are less ideal since they are present in much lower abundance.

A further unexpected advantage is that the rRNAs (and the genes encoding them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

Additionally, the present invention provides probes to Salmonella rRNA target sequences which are sufficiently similar in a significant number of Salmonella that one or a few probes can hybridize to the target region in all such Salmonella. Advantageously, these same rRNA target sequences are sufficiently different in most non-Salmonella rRNAs that, under the preferred assay conditions of the present invention, the probe(s) of the present invention hybridize to Salmonella rRNAs and do not generally hybridize to non-Salmonella rRNAs. These probe characteristics are defined as inclusivity and exclusivity, respectively. The discovery that probes could be generated with the extraordinary inclusivity and exclusivity characteristics of those of the present invention with respect to Salmonella was unpredictable and unexpected.

In a particularly preferred embodiment of the invention, an assay method for detecting Salmonella is provided in which bacteria in the sample to be tested are preferably grown for a limited time under conditions which foster rapid and abundant growth of any Salmonella in the sample and which are biased against the growth of many closely related bacteria. Hybridization analysis using the preferred probes of the present invention is then advantageously performed on the sample after this growth period.

BRIEF DESCRIPTION OF THE FIGURE AND TABLES

Further understanding of the principles and aspects of the present invention may be made by reference to the figures and tables wherein:

FIG. 1—Shows the target hybridization sites of the preferred probes of the present invention. A schematic illustration of the relevant portions of the *E. coli* 23S rRNA, folded into its proposed (conserved) secondary structure, is shown.

Nucleotide residues are numbered (using the *E. coli* numbering convention) from the 5' terminus of the rRNA. The target sites of Salmonella probes 849, 1069, 1165, 1166, and 1200 are shown to illustrate their proximity to one another.

Table 1 Shows alignment of the nucleotide sequences of the preferred probes of the present invention with the nucleotide target sequences of a number of Salmonella strains along with relevant portions of the 23S rRNAs from a number of closely related non-Salmonella bacteria. RNA sequences are written 5' to 3', probe sequences are DNA and written 3' to 5'. Lower case C (c) in certain of the probes indicates a modified cytosine residue to which a reporter group may or may not be attached depending on the assay format employed. Probes 1165, 1200, 1166, 1069 and 849 are shown, along with the "core" region of variation upon which they are based. Probes 1166 and 1069 were designed to be used as detector probes in conjunction with any or all the capture probes 1165, 1200, and 849 probes.

Table 2 Exemplifies the inclusivity behavior of the preferred probes toward a representative sampling of Salmonella strains in dot blot and liquid hybridization assays.

Table 3 Exemplifies the exclusivity behavior of the preferred probes toward a representative sampling of non-Salmonella strains.

Table 4 Provides data showing detection of Salmonella in food samples with the preferred probes in a preferred format of the present invention.

DETAILED DESCRIPTION OF THE INVENTION AND BEST MODE

Probe Development Strategy

Figure 1:
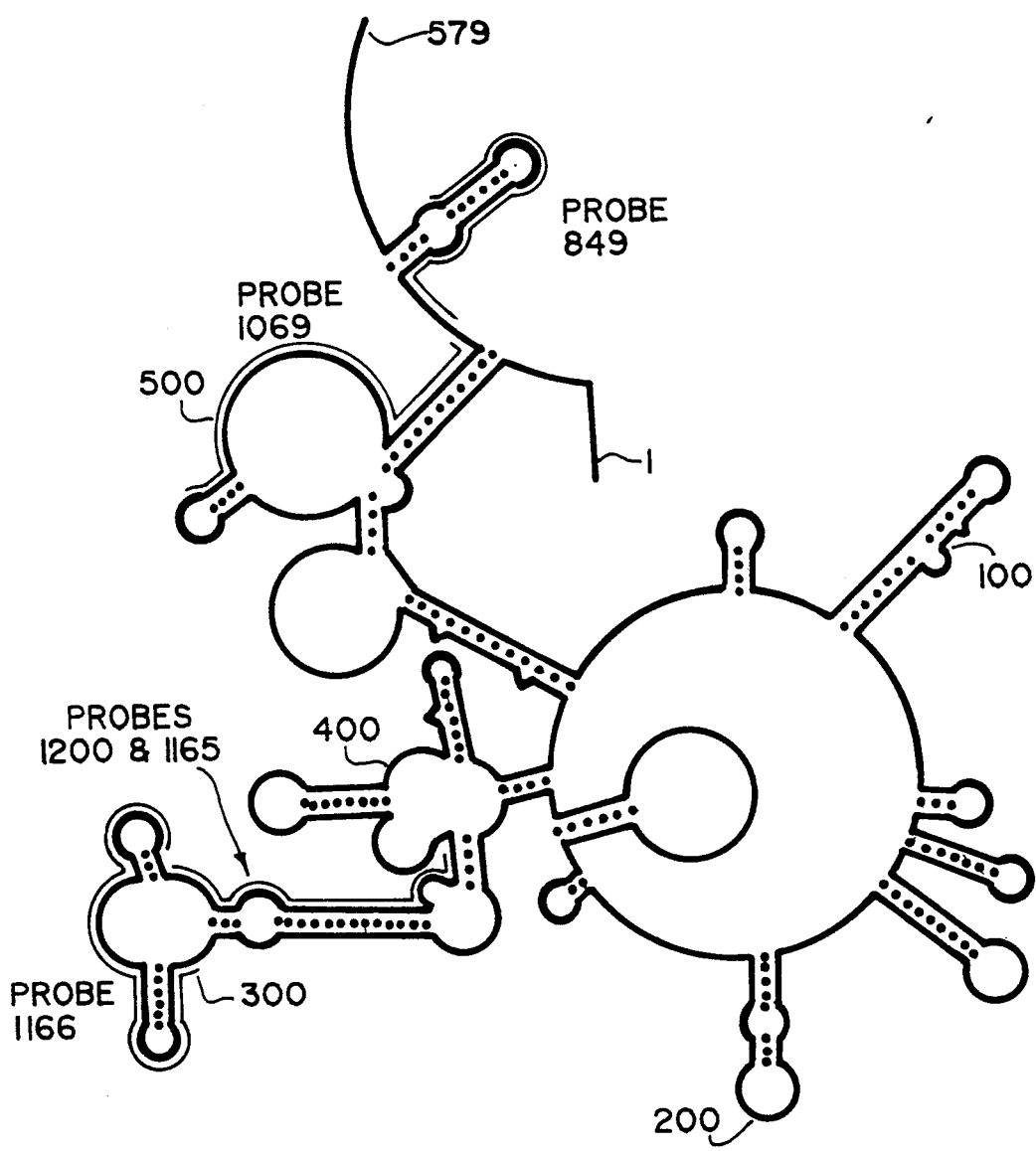

The probes of the present invention were developed utilizing the strategy outlined in U.S. Ser. No. 127,484. Briefly, 16S and 23S rRNA sequences from a representative collection of Salmonella and closely-related non-Salmonella bacteria were determined by standard laboratory methods. Representative Salmonella were selected initially on the basis of reported DNA (whole genomic) similarities among Salmonella. Six major groupings of Salmonella have so far been defined. During the course of these efforts, the more relevant rRNA homologies among Salmonella could be used to define groupings based on accumulating rRNA sequence information and results of hybridization experiments with initial test probes. Of the non-Salmonella genera inspected, Citrobacter, Escherichia, Klebsiella and Enterobacter were determined to be of particular importance because they: 1) are among the most closely related enterobacteriacae to Salmonella, 2) have been found to most often share similar patterns of 16S and 23S sequence conservation with at least some Salmonella, 3) are frequently found to cohabit the same environments as Salmonella and 4) frequently grow to much higher abundance than Salmonella in these environments. Therefore, their discrimination is both important and difficult.

(described below). Some 350 Salmonella strains and 100 non-Salmonella strains routinely were used to assess the hybridization behavior of individual probes and probe sets. In addition, large numbers of food and environmental isolates of Salmonella and non-Salmonella bacteria were tested with the most promising probes.

The foregoing probe selection strategy yielded a number of additional, improved probes useful for identifying Salmonella bacteria in samples—not described in U.S. Ser. No. 127,484. Specifically, all the probes of the present invention are directed against (i.e. specifically hybridize to) target regions located in Salmonella 23S rRNA. The location of these target sequences and their relative proximity to one another is shown in the Figure. Probe and target sequences are given in Table 1. The hybridization behavior of the probes and probe sets toward Salmonella and non-Salmonella bacteria are detailed in Tables 2, 3, and 4.

Physical Description of Probes

The following oligonucleotide probes are disclosed herein:

| Probe 849: | 5'-ACACAGGTAAACCTGTGCTCCCACTGCT |
| Probe 1165: | 5'-AGCTCACAGCACATGCGCTTTTGTGTAC |
| Probe 1200: | 5'-AGCTCACAGCATATGCGCTTTTGTGTAC |
| Probe 1166: | 5'-cGCTGTCACCCTGTATCGCGCGCCTTTCCAGACGCTTcT |
| Probe 1069: | 5'-cTACGTACACGGTTTCAGGTTCTTTTTCACTCCCCTcT |

Regions of potentially useful variation between Salmonella and non-Salmonella rRNA sequences are defined as those which share specific or highly related sequences among all or some Salmonella and exhibit significant differences between Salmonella and non-Salmonella bacteria. Such regions of potentially useful variation between Salmonella and non-Salmonella rRNA sequences were identified by computer-assisted comparisons of available Salmonella and non-Salmonella rRNA sequences. 'Highly related' and 'significant differences' then are operationally verified by hybridization experiments in which synthetic oligonucleotides complementary to the Salmonella sequences are used to probe panels of Salmonella and non-Salmonella bacteria.

Under given hybridization conditions, each probe will have a characteristic hybridization profile versus the tested bacteria. Ideal target sequences which are highly related among Salmonella and significantly different in non-Salmonella yield probes that are highly inclusive and exclusive.

Oligonucleotide probes complementary to (i.e. capable, under defined conditions, of specifically hybridizing to) various potentially useful Salmonella rRNA target sequences were designed based on principles outlined in U.S. Ser. No. 127,484, that is with consideration of: 1) the secondary structure of the rRNA target site, 2) the potential inter- and intra-molecular interactions of the probe with itself and other probes that might simultaneously be used in the assay, 3) the assay format itself. The probes were conveniently synthesized by standard phosphoramidite techniques (Caruthers, M. H. et al. [1983], in Gene Amplification and Analysis, eds. Papas, T. S., Rosenberg, M., and Charikjian, J. G., Pub. Elsevier, N.Y., Vol. 3 pp. 1–26) on an Applied Biosystems instrument.

The behavior of designed probes then was evaluated by hybridization assays in which extensive panels of Salmonella and non-Salmonella bacteria were tested Probes 849, 1165, and 1200 are designed to preferably serve as "capture" probes in the preferred liquid hybridization assay described in Example 1—General. In this use they will have appended to their 3' termini a string of ca. 50–200 deoxyadenosine (dA) residues with which they can be "captured" (along with the rRNA target molecule to which they are hybridized) to a polydeoxythymidine (poly-dT) coated solid support. Probes 1166 and 1069 are designed to ideally serve as "detection" probes. The lower case C (c) in the above indicated sequences of probes 1166 and 1069 designates a chemically modified cytosine residue to which a detection ligand may or may not be attached, depending upon the assay strategy (see below, Example 1). The 3' terminal T on this oligonucleotide is a technical convenience of the synthetic addition of these modified C residues and is not necessarily complementary to the target nucleotide sequence. All probes of the present invention are complementary to (i.e. preferentially hybridize to) target sequences within the 23S rRNA molecules found in Salmonella bacteria.

Probes 1165, 1166, 1069, and 849 are complementary to (i.e. specifically hybridize to) the version of their target sequence which was found in Salmonella typhimurium strain ATCC 23566 (Table 1).

Probe 1165 hybridizes specifically to a large subset of, but not all, Salmonella bacteria (Tables 2 and 3).

Probes 1166 and 1069 hybridize to nearly all Salmonella tested but also hybridize to some non-Salmonella bacteria (Tables 2 and 3). In spite of this less than ideal exclusivity behavior, probes 1166 and 1069 exhibit a number of very useful characteristics when used in conjunction with capture probes 1165, 1200 and 849 and can significantly enhance the behavior of those probes in certain assay formats (described below).

Probe 1200 is the same length as probe 1165 and hybridizes to the same target position in the Salmonella 23 S rRNA (Figure, Table 1). However, probe 1200 is of slightly different sequence composition than probe 1165 (see Table 1) and instead is complementary to the *Salmonella typhi* (strain RF 755) version of the sequence occurring in that target region. Upon hybridization testing, it was surprisingly discovered that this minor sequence difference has significant effects on the behavior of the probe toward Salmonella bacteria. Specifically, probe 1200 exhibits advantageously broader hybridization among Salmonella strains than probe 1165 and, in fact, hybridizes as well as probe 1165 to the 23 S rRNA of *Salmonella typhimurium*.

Probe 849 was described in U.S. Ser. No. 127,484, and is reviewed here because it has turned out to have newly discovered utility as part of probe sets comprising some or all of the other probes of the present invention (discussed below).

The specific behavior of probes 849, 1069, 1165, 1169 and 1200 are dependent to a significant extent on the assay format in which they are employed. Conversely, the assay format will dictate certain of the optimal design features of particular probes. The "essence" of the probes of the invention is not to be construed as restricted to the specific string of nucleotides in the named probes 849, 1069, 1165, 1166, and 1200. For example, the length of these particular oligonucleotide probes was optimized for the particular assay format in which they are employed. It is well known to one skilled in the art that optimal probe length will be a function of the stringency of the hybridization conditions chosen and hence the length of the instant probes may be altered in accordance therewith. Also, in considering sets comprised of more than one probe, it is desirable that all probes behave roughly equivalently under one given hybridization format. Thus, the exact length and composition of a particular probe will to a certain extent reflect its specific intended use.

The "essense" of the probes described herein resides in their utilization of "Salmonella-specific" sequences. In general, this centers around a "core region" discovered within the actual target sequence of particular 23 S rRNA nucleotide positions. The core regions upon which probes 849, 1165, and 1200 are based are indicated in Table 1. These core regions and the significance of other physical aspects of the probes are discussed further below following introduction of the hybridization assays.

Hybridization analyses of probe behavior

Hybridization behavior of the probes toward representative Salmonella and non-Salmonella bacteria was determined in two basic ways. Initial screening of potentially useful probes was accomplished by dot blot analysis. Further useful inclusivity and exclusivity information as well as specific reduction to practice in a "user-friendly" format was accomplished by liquid hybridization analyses (Tables 2, 3, and 4).

"Dot blot" analysis, in accordance with well known procedures, was employed to preliminarily test the inclusivity and exclusivity properties of first generation probes. As is known, dot blot analysis generally involves immobilizing a nucleic acid or a population of nucleic acids on a filter such as nitrocellulose, nylon, or other derivatized membrane which can be readily obtained commercially, specifically for this purpose. Either DNA or RNA can be easily immobilized on such a filter and subsequently can be probed or tested for hybridization under any of a variety of nucleic acid hybridization conditions (i.e., stringencies) with nucleotide sequences or probes of interest. Under stringent conditions, probes whose nucleotide sequences have greater complementarity to the target sequence will exhibit a higher level of hybridization than probes containing less complementarity. For the oligonucleotide probes described herein, (e.g., preferably 30–36 nucleotides in length and of average base composition) hybridization to rRNA targets at 60° C., for 14–16 hours (in a hybridization solution containing 0.9M NaCl, 0.12M TrisHCl, pH 7.8, 6 mM EDTA, 0.1M KP04, 0.1% SDS, 0.1% pyrophosphate, 0.002% ficoll, 0.02% BSA, and 0.002% polyvinylpyrrolidine) followed by three, 15 minute post-hybridization washes at 60° C. to remove unbound probes (in a solution containing 0.03M NaCl, 0.004M Tris-HCl, pH 7.8, 0.2 mM EDTA and 0.1% SDS), would be sufficiently stringent to produce the levels of specificity and sensitivity demonstrated in the tables and examples. Techniques also are available in which DNA or RNA present in crude (unpurified) cell lysates can be immobilized without having to first purify the nucleic acid in question (referred to herein as cytodots (see for example Maniatis, T., Fritsch, E. F. and Sambrook, J. (1982) Molecular Cloning, a Laboratory Manual). This latter approach was found to significantly decrease the amount of effort required to screen for particular nucleotide sequences which may be present in the nucleic acids of any particular organism and, moreover, is advantageously amenable to the mass screening of large numbers of organisms. It, therefore, is a preferred method for exclusivity and inclusivity screening of potential nucleic acid hybridization probes vs. large numbers of organisms.

Tables 2 and 3 show the dot blot hybridization patterns of probes 849, 1165, 1166 and 1200 to some 350 Salmonella and 85 closely-related non-Salmonella bacteria. Also shown in Tables 2 and 3 are results of liquid hybridization experiments using the probes of the invention in a preferred assay format to detect diluted samples of pure cultures of many of these same Salmonella and non-Salmonella bacteria. Example 1—General, describes the basic assay, including examples of the range of possible variation for some assay steps, which was used to generate the liquid hybridization, inclusivity and exclusivity data shown in Tables 2 and 3. Example 1-Specific, is a specific application of the assay and one of the preferred probe sets on selected Salmonella strains "spiked" into a variety of food samples. The data from this experiment is shown in Table 4.

EXAMPLE 1

General: A Homopolymer Capture, Dual Probe, Liquid Hybridization Format

Cultures containing Salmonella and/or non-Salmonella bacteria were grown in appropriate broth, then the nucleic acids were released by any of a number of appropriate lysis agents (e.g., NaOH, Guanidine salts, detergent, enzymatic treatment, or some combination of the aforementioned). Hybridization was carried out with two different probes or probe sets at least one of which, but not necessarily both, must be specific for the organisms to be detected. In this example, one or all of the Salmonella specific "capture" probes, 849, 1165 and 1200, were enzymatically tailed with 20–200 deoxyadenosine (dA) residues at their 3' termini, and one or both of the reporter probes, 1069 and 1166, were labeled either chemically or enzymatically with radioactive Phosphorous (P-32) or other small ligand (e.g., fluorescein or biotin) which was used to detect the captured target molecules. (Various specific probe sets are indicated in Tables 2 and 3).

Generally, following cultivation/enrichment of the bacteria present in the test samples, small aliquots of the cultures were transferred to test tubes. The bacteria were lysed, the capture and detection probes (diluted in an appropriately concentrated stock of hybridization solution) were added, and hybridization was allowed to proceed at any appropriate temperature for an appropriate period of time (see below, Example 1—Specific). The solution containing the target/probe complex then was brought into contact with a surface containing bound poly-deoxythymidine (poly-dT) homopolymer (1500-4000 nucleotides in length), under conditions that allowed hybridization between the dA and dT.

In this example, poly-dT was bound to a plastic "dipstick" which was submerged in the target/probe solution. If Salmonella ribosomal RNA was present in the test sample, one or more of the dA tailed, Salmonella-specific capture probes would have hybridized to the target rRNA sequences present and, in turn, would be captured onto the dipstick. Unhybridized nucleic acids and cellular debris were washed away, leaving the captured DNA-RNA complex attached to the surface via the dA-dT duplex. The reporter probe also was bound to the dipstick via the chain of interactions—Capture surface-dT: dA-Capture probe:Target:Reporter Probe—only if the correct target nucleic acid was present. The bound, ligand derivatized (e.g., fluoresceinated in this example, or biotinylated, etc.) reporter probe then was detected by the addition of an anti-ligand antibody:enzyme complex (e.g., anti-fluorscein:horseradish peroxidase in this example, or streptavidin:horseradish peroxidase, etc.). Following incubation under conditions permitting specific binding of the detection complex, washing to remove non-bound enzyme, addition of chromogenic substrate and subsequent color development (typically 20-30 minutes), and the optional addition of color-termination solution, the developed color was measured spectrophotometrically. This reading (typically in the range of 0.1→2.0 O.D. units) was compared to the negative control levels, a threshold or cutoff value established, and a determination of the "significance" of the experimental levels made. Tables 2 and 3 show the results of a number of such experiments, using pure cultures of various Salmonella (Table 2) and non-Salmonella (Table 3) bacteria and various combinations of the probes of the present invention.

Do blot and liquid hybridization data are presented side by side in Tables 2 and 3 in order to facilitate comparisons between the two.

Both inclusivity (Table 2) and exclusivity (Table 3) dot blot experiments employed approximately the same number of target organisms, the same levels of probes, and identical hybridization conditions (described above). Thus, the dot blot inclusivity pattern shown in Table 2 for each of the Salmonella-specific probes pertain to assay conditions under which the probes show little or no hybridization to equivalent numbers of non-Salmonella bacteria.

Liquid hybridization data was recorded for various probes and probe sets on a subset of the Salmonella and non-Salmonella bacteria tested using the dot blot procedure. In the liquid hybridization experiments, probes were tested against 1:100 dilutions of stationary phase Salmonella cultures (corresponding roughly to ten million Salmonella per millimeter). Exclusivity data was generated by testing of the probes and probe sets against UNDILUTED stationary phase cultures of the indicated non-Salmonella bacteria. Thus, the liquid hybridization data was biased toward documenting the behavior of the assay and probes under the unfavorable circumstance where a test sample contains low levels of Salmonella bacteria and 100 fold higher levels of non-Salmonella bacteria.

Most of the non-Salmonella listed as ND (not determined) in the liquid hybridization portion of Table 3 actually have been tested under lower stringency conditions of hybridization than those used to generate the data shown in Tables 2 and 3. These were at or near background levels (0-0.1 OD 450). The liquid hybridization data actually shown in Table 3 corresponds, for the most part, to non-Salmonella bacteria which gave unacceptably high signals under the initial low stringency hybridization conditions, and which then were retested using the higher stringency conditions ultimately adopted for the assay. It therefore is expected that all non-Salmonella strains listed in Table 3 will yield little or no signal in the preferred assay format. This conclusion also is strongly supported by the high level of concordance between dot blot and liquid hybridization results as indicated in the Tables.

Finally, it is worth noting that the Salmonella strains listed in Table 2 are listed in order of their relative clinical incidence according to statistics provided by the Atlanta Centers for Disease Control (1985) with the most frequently isolated Salmonella listed first. The 100 most commonly isolated strains account for about 93.3% of all Salmonella isolated in the United States (CDC, 1985). The remaining 6.7% of isolates are spread across approximately 2,000 known Salmonella strains. The behavior of probes and probe sets of the present invention may be summarized as follows.

Exclusivity—None of the probes of the present invention (with the expected exceptions of probes 1166 and 1069) hybridizes, in the described assay formats, to any significant extent with any non-Salmonella bacteria tested. This highly desirable property of the probes is very important in defining the overall utility of the probes and assays which employ them, and has been examined in great detail. The bacteria listed in Table 3 represents a very carefully selected panel of strains which encompass: 1) the full known genotypic breadth of the genera most closely related to Salmonella, and 2) those genera which most frequently are encountered in food samples which routinely are tested for Salmonella contamination. In addition to these pure culture tests, numerous cultures of food and environmental samples were tested using the probes and assays to ensure that naturally-occurring, non-Salmonella contaminants of these samples would not react with the probes in the preferred assay formats. Only a representative sample of this extensive testing is shown in Table 4.

Inclusivity—Detailed documentation of the inclusivity behavior of individual probes and of certain sets of probes is given in Table 2. The table obviously is quite large and complex; but was deemed necessary to adequately describe the expected behavior of various probes and probe combinations of the present invention. An attempt to succinctly summarize the data shown in Table 2 is made below.

In interpreting this data, bear in mind that for the dot blots the hybridization behavior of each probe is tested individually. That is, a probe either hybridizes at some measurable level to the rRNA of the tested bacterium or it does not. For the liquid hybridization data, at least two probes must hybridize to the target rRNA in order for a signal to be detected. One or more capture probes must hybridize to the rRNA in order to bind the rRNA to the solid support (poly-dT coated dipstick) and, in addition, one or more detection probes also must bind to the same target molecule. Thus a positive liquid hybridization result indicates that both a capture and detection probe bind to the rRNA target of the test bacterium, but a negative result indicates only that either the capture probe or the detection probe or both do not bind. The cause of a negative liquid hybridization result can be inferred by inspecting the hybridization behavior of other probe combinations in the liquid hybridization format or by inspecting the dot blot results of individual probes. In this fashion, the data in Table 3 either explicitly documents or can be used to infer the inclusivity behavior for various combinations of probes of the present invention in the preferred sandwich-type, liquid hybridization assay format described above.

Probe 1165 (capture)/probe 1166 (detection)—This combination detects 323 out of 357 Salmonella tested and no non-Salmonella bacteria. It thus is a quite useful probe set but has the shortcoming for some potential applications that it is not as fully inclusive for all Salmonella as is the most preferred embodiment. This probe set also detected only weakly *S. typhi* which has a relatively high incidence of isolation as a food contaminant in the United States. Inspection of the dot blot data indicates that the less than optimal hybridization of this probe set to *S. typhi* strains is attributable to poor hybridization by the 1165 probe. The sequence data shown in Table 1 also predicts this less than optimal hybridization behavior of probe 1165 to *S. typhi* since a C:A mispair can be seen to exist near the center of this probe/target hybrid.

Probe 1200 (capture)/probe 1166 (detection)—This combination detects 353 out of 366 Salmonella tested and no non-Salmonella bacteria. As discussed above, probe 1200 hybridizes to the same region of Salmonella 23S rRNA as probe 1165, but is specifically complementary to the *S. typhi* version of this semi-conserved target sequence. As demonstrated by the data in Tables 2 and 3, probe 1200 is highly specific for Salmonella. Unexpectedly, it hybridizes much more broadly among Salmonella than probe 1165 and is therefore more preferred.

The reason for the different hybridization behavior of probes 1165 and 1200 can be seen in the nucleotide sequence data shown in Table 1. Probe 1200 is perfectly complementary to its target region in *S. typhi* and but also is complementary to the homologous target region in *S. typhimurium* if one allows a single, non-canonical G:T base pair. The G:T base pairs can contribute at least some energy to a nucleic acid helix is well established in the literature. But it could not have been predicted that this would have permitted probe 1200 to hybridize to more Salmonella than probe 1165 because the sequences through this 23S rRNA region are not known for the vast majority of Salmonella.

Furthermore, it could not be predicted that probe 1200 would not also disadvantageously cross hybridize to non-Salmonella by virtue of this G:T pairing.

Of the simple (one capture/one detector) probe combinations, the probe set 1200/1166 hybridizes to the most Salmonella while also exhibiting no hybridization to non-Salmonella. The few Salmonella not detected by the 1200/1166 probe set (e.g. *S. flint* and the Group V Salmonella) occur only rarely, so the 1200/1166 combination is quite useful in assays intended to detect Salmonella in most food, clinical or environmental samples. However, a probe set which will impart 100% inclusivity for Salmonella to an assay also is highly desirable.

The following, more complex and more preferred probe sets build on the 1200/1166 set in order to provide such inclusivity. Probe 1165 may be added to the "base" 1200/1166 set in order to detect *S. flint* and also to enhance the signal obtained with a few other Salmonella strains to which the 1165 probe hybridizes slightly better than the 1200 probe (e.g. *S. paratyphi* B, strain RF635). Capture probe 849 may be added to detect the group V Salmonella. Finally, because the Group V Salmonella do not, for the most part, hybridize well with the 1166 detection probe, an additional detection probe, probe 1069, may be included along with probe 849 to increase the detection sensitivity of the group V Salmonella.

Tables 2 and 3 provide representative hybridization data for various useful combinations of the just-described probes. The most preferred combination of capture probes 1200, 849, and 1165 collectively hybridize to all 380 tested strains of Salmonella (Table 2) and no non-Salmonella (Table 3). Probes 1166 and 1069 are less Salmonella-specific but as a pair also hybridize to all Salmonella. In the most preferred sandwich-type liquid hybridization assay described herein (Example 1—General), the set of homopolymer-tailed, "capture" probes 1200, 849, and 1165—combined with labeled "detection" probes 1166 and 1069—detect all 380 tested strains of Salmonella and no non-Salmonella.

The assay is quite sensitive. At hybridization stringencies sufficient to completely suppress all detectable hybridization to saturated cultures of non-Salmonella bacteria (up to ca. $10^9$ bacteria/ml for Citrobacter species), the assay can detect the presence of between $10^5$–$10^6$ Salmonella. This concentration of Salmonella is achieved readily and reproducibly in enrichment cultures inoculated with naturally Salmonella-contaminated food and environmental samples as demonstrated below (Example 1-Specific).

EXAMPLE 1

Specific: Detection of Salmonella inoculated into food samples.

Twenty food types were tested. They were selected because they represent a variety of product types that require different pre-enrichment conditions, and because each has been implicated as a potential source of Salmonella. The strains used to inoculate the food samples represent serovars specifically isolated from each food type (Flowers et al., 1987). Twelve samples from each food type were inoculated with approximately 50 colony-forming units (CFU) of Salmonella per gram (High inoculum), twelve samples were inoculated with 5 CFU/gram (Low inoculum), and six samples were uninoculated controls.

For all food samples, culture enrichment and culture identification (reference method) were done according to methods prescribed by the F.D.A. (FDA/BAM Bacteriological Analytical Manual, Chapter 7, 6th Edition, 1984, Supplement 9/87, Association of Official Analytical Chemists). According to these procedures, the culture enrichment scheme occurs in three steps: (1) pre-enrichment of 25 gram food samples in various broths specific for each food type; (2) selective enrichment—samples from each pre-enrichment culture are each inoculated into a tube of Selenite Cysteine Broth, and a tube of Tetrathionate Broth; and (3) post-enrichment—samples from each selective enrichment culture are each inoculated into separate tubes of Gram Negative (GN) Broth. Two GN broth cultures are thus obtained from each food sample.

To assay the cultures, 0.25 ml from each of the two GN broth cultures obtained above were combined in a test tube. The bacteria were lysed by treatment with 0.1 ml lysis solution (NaOH, 0.75N) and incubated at room temperature (15°-30° C.) for five minutes. The bacterial lysates were neutralized by the addition of 0.1 ml of neutralization buffer (2M Tris. HCl, pH 7.0), and then heated in a 65° C. water bath for 15 minutes. The nucleic acids released from each sample were detected by addition of 0.1 ml of specific capture and detector probe sets (preferably containing between 1.75 and 3.15 microgram/ml of preferred capture probe set 1165/1200 and 2-4 microgram/ml of detector probe 1166 in the experiment shown in Table 4; although other combinations and amounts of probes may be used). The mixtures were incubated in a 65° C. water bath for 15 minutes to enable hybridization of the specific capture and detector probes (DNA) to target nucleic acids (rRNA) to take place. Poly-dT coated capture dipsticks were placed into the test tubes containing the DNA/rRNA hybrids and further incubated at 65° C. for 60 minutes to capture the hybrids onto the dipsticks.

After hybridization, the dipsticks were washed by dipping them into a wash basin containing enough wash solution held at 65° C. to cover the reactive part of the dipstick (50 mM Tris, pH 7.5, 150 mM NaCl, 2 mM EDTA, and 0.1% Tween 20) for 1 minute. This process was then repeated in fresh solution at room temperature.

The washed dipsticks were removed from the wash basin, blotted dry with absorbent paper, placed into a set of test tubes containing 0.75 ml antibody-enzyme conjugates (antifluorescein antibody:horseradish peroxidase diluted in wash buffer), and allowed to incubate at room temperature for 20 minutes.

After allowing the antigen-antibody reaction to occur, the dipsticks were removed from the test tubes, washed twice at room temperature and blotted in the same manner as described in the preceding two paragraphs. The dipsticks were placed into a set of labelled test tubes containing substrate-chromogen mixtures and allowed to incubate at room temperature for 20-30 minutes. The dipsticks were then removed and the color development step terminated by the addition of 0.25 ml 4N sulfuric acid. The optical density of the samples was measured spectrophotometrically at 450 nm.

Sample tubes with O.D. values greater than 0.1 were considered positive for Salmonella, those with lower O.D. values indicated the absence of Salmonella. Table 4 contains a representative sample of the data generated with the 20 food types. All 40 inoculated samples and one uninoculated control (Nonfat dry milk) were positive by both the hybridization and reference assays. Nine of the ten uninoculated controls were consistently negative by both methods. Overall, both methods agreed in 589 of 600 food samples tested in the study.

While the description of the invention has been made with reference to detecting rRNA, it will be readily understood that the probes described herein and probes complementary to those described herein will also be useful to detect the genes (DNA) encoding the rRNA and accordingly, such probes are to be deemed equivalents to the described probes and encompassed within the spirit and scope of the present invention and the appended claims.

TABLE 1

PROBES AND 23S RIBOSOMAL RNA TARGET SEQUENCES

| Position # | 299 | 314 | 338 | 348 | 357 | 365 |
|---|---|---|---|---|---|---|

```
Escherichia coli           5'...GGAAGC—GUCUGGAAAGG—CGCGCGAUACAGGGUGACAGCCCCGUACACAAAAUGCACAUGCUGUGAGCUCGA...
Probe 1166                      TcTTCG—CAGACCTTTCC—GCGCGCTATGTCCCACTGTCGc-5'
Probe 1200                                                                          CATGTGTTTTCGCGTATACGACACTCGA-5'
Probe 1165                                                                          CATGTGTTTTCGCGTACGACACTCGA-5'
Core Variation                                                                      **********
Salmonella typhimurium     ...GGAAGC—GUCUGGAAAGG—CGCGCGAUACAGGGUGACAGCCCCGUACACAAAAGCGCAUGCUGUGAGCUCGA...
Salmonella arizona 1       ...GGAAGC—GUCUGGAAAGG—CGCGCGAUACAGGGUGACAGCCCCGUACACAAAAGCGCAUGCUGUGAGCUCGA...
Salmonella typhi 1         ...GGAAGC—GUCUGGAAAGG—CGCGCGAUACAGGGUGACAGCCCCGUACACAAAAGCGCAUGCUGUGAGCUCGA...
Salmonella typhi 2         ...GGAAGC—GUCUGGAAAGG—CGCGCGAUACAGGGUGACAGCCCCGUACACAAAAGCGCAUGCUGUGAGCUNGA...
Salmonella strasbourg      ...GGAAGC—GUCUGGAAAGG—CGCGCGAUACAGGGUGACAGCCCCGUACACAAAAGCGCAUGCUGUGAGCUCGA...
Salmonella freetown        ...GGAAGC—GUCUGGAAAGG—CGCGCGAUACAGGGUGACAGCCCCGUACACAAAAGCGCAUGCUGUGAGCUCGA...
Salmonella djakarta        ...GGAAGC—GUCUGGAAAGG—CGCGCGAUACAGGGUGACAGCCCCGUACACAAAAGCGCAUGCUGUGAGCUCGA...
Salmonella wassenaar       ...GGAAGC—GUCUGGAAAGG—CGCGCGAUACAGGGUGACAGCCCCGUACACAAAAGCGCAUGCUGUGAGCUCGA...
Salmonella daressalaam     ...GGAAGC—GUCUGGAAAGG—CGCGCGAUACAGGGUGACAGCCCCGUACACAAAAGCGCACAUGYUGUGAGCUCGA...
Salmonella brookfield      ...GGAAGU—GUCUGGAAAGG—CACGCGAUACAGGGUGACAGCCCCGUACACGAAAAUGCACCUGCUGUGAGCUCGA...
Salmonella bongor          ...GGAAGU—GUCUGGAAAGG—CGCGCGAUACAGGGUGACAGCCCCGUACACACAAAAUGCACAUGCUGUGAGCUCGA...
Salmonella sp. CDC N55     ...GGAAGC—GUCUGGAAAGG—CGCGCGAUACAGGGUGACAGCCCCGUACACNAAAAUGCACCUNNUGAGCUYNA...
Citrobacter diversus       ...GGAAGC—GUCUGGAAAGG—CGCACGCGAUACAGGGUNAAAGUCCCGUACACAAAAUGCACAGGCUNUGAGCUCGA...
Citrobacter freundii 1     ...GGAAGC—GUCUGGAAAGG—CGCGCGAUACAGGGUGACAGCCCCGUACACAAAAUGCACAUUGUGAGCUYGA...
Shigella dysenteriae       ...GGAAGU—GUCUGGAAAGG—CGCGCGAUACAGGGUGACAGCCCCGUACACAAAAUGCACAUAUUGUGAGCUNNA...
Yersinia enterocolitica    ...GGAAGC—GUCUGGAAAGU—CGCACGCGAUACAGGGUGAUAGCCCCGUACGCUNAAAAUGCAUACGUGUGAGCUCGA...
Proteus vulgaris           ...AGAACA—GUCUGGAAAGC—UNGCCRCAGCAGGGUGAUNAAGGYNUNUNGUNUNUNGAGUUCNC...
Pseudomonas aeruginosa     ...GGAACG—CUCUGGAAAGU—GCGGCAUAUGGGUGAUAGCCCGUACGCUCAAAG—G—AU—CUUUGAAGUGAAAU...
Bacillus subtilis          ...UGAAGAGGUCUGGAAAGGGCCCCCCAUAGGAGGUAACAGCCCUGUAGUCGAAAACUUCCUCCUCUCGAGUGGA...
Anacystis nidulans         ...CGAAGC—AGCUGAAAACU—GCACCAGAGAAGGUGAAACCGUGUACGUACAGCAGUGCACAUGCACU—CCUAGCUGAA...
```

| Position # | | | 492 | 526 529 | 541 | 554 |
|---|---|---|---|---|---|---|

```
Escherichia coli           ...CGAGGGGAGUGAAAAGAACCUGAAACCGUGUACGUACAAGCAGUGGGAGCAC—GCUU——AGGCGUGUGAC...3'
Probe 1069                      TcTCCCCCUCACUUUUCUUGGACUUUGGCACAUGcCATc-5'
Core Variation                                                                   TCGUCACCCUCGUCCAA—ATGACACA-5'
                                                                                 ***********
Salmonella typhimurium     ...AAAAGAACCUGAAACAGUGAAAANGAACCUGAAACAGUGAAACAAGUAGAGUUGAGCAGUAGUU—UACCUGCAUGAC...
Salmonella arizona 1                                     GAACCUSAAACCGUGAAACCUGUACGUACAAGCAGUGGGAGCCU—UUCGUCAGUGAC...
Salmonella arizona 2                                                                                  
Salmonella brookfield      ...CGAGGGGAGUGAAAAGAACCUGAAACCGUGUACGUACAAGCAGUGGGAGCCU——CUU——UNCCUGUGAC...
Salmonella sp. CDC N55     ...CGAGGGGAGUGAAAAGAACCUGAAACCGUGUACGUACAAGCAGUGGGAGCCU——UACCUGUGAC...
Salmonella djakarta                                      CCGUGUAACCGUGUACGUACAAGCAGUGGGAGCAC———CUU——NGGGGUGAC...
Salmonella oranienburg                                                     CGUACAACCGUGUACGUACAAGCAGUGGGAGCAC———CYU——NNGGGGUGAC...
Citrobacter freundii 2                                                                                CGUACAACCGUGUACGUACAAGCAGUGGGAGCCU———CUU——UAUGGGUGAC...
Citrobacter freundii 3                                   CGAGGGNGUGAAAANGAACCUGAAACCGUGUACGUACAAGCAGUGGGAGCAC——CG—GGUUUGAC...
Shigella dysenteriae                                                                                  CGUACAAACCGUGUACGUACAAGCAGUGGGAGCCU——CUU——UAUGGGUGAC...
Enterobacter sakazaki                                                          CCGUGUAAACCGUGAAACCUGAAAUAGAACCUGAAACGGAAGGCACGAGUU———CUU———AAGAGGUYGAC...
Yersinia enterocolitica                                                                CCGUGUAAACCUGAAACCUGUAUGCGUACAAGCAGUGGGAGCAC——CNU——CGUGGUSYSAC...
Pseudomonas aeruginosa     ...CGAGGGGCCGUGAAGUGAAAAUAGAACCUGAAACGGUGUACGUACAAGCAGUGGGAGCCU—ACUU———GUUAGGUGAC...
Bacillus subtilis          ...AGAGGGAGUGAAAAGAGAUCCUGAAACCGUGUGAGCCUAACAAGUAGUCAGAGCCC——GUUA———ACG—GUGAU...
Anacystis nidulans         ...A—AGGGGAGUGAAAAUAGAACAUGAAAACCGUGUACGGACCUAACAAGUAGCAGUGCGAGCCC——GAUU——CAACGGUGAC...
```

Symbols used:

(...) = sequence continues but is not presented; (—) = corresponding nucleotide is not present in that sequence but sequence is continuous;
N = C, A, G or U; K = G or U; R = A or G; Y = C or U; S = C or G.

TABLE 2

SALMONELLA INCLUSIVITY DATA

| SALMONELLA SEROVAR | TYPE | STRAIN | SOURCE | DOT BLOT HYBRIDIZATION PROBES | | | | LIQUID HYBRIDIZATION | | | | | | |
|---|---|---|---|---|---|---|---|---|---|---|---|---|---|---|
| | | | | 1165 | 1200 | 849 | 1166 | 1166/1165 | 1166/1200 | 1166/1165/1200 | 1166/849 | 1166/1200/849 | 1166/1165/1200/849 | 1069/1166/1200/849 |
| TYPHI-MURIUM | B | 654 | (1) | ++++ | ++++ | ++++ | +++ | 1.46 | 1.90 | 2.00 | ND | 1.76 | 0.71 | ND |
| | | 23566 | (6) | ++++ | +++ | ++++ | ++ | ND | 1.07 | ND | ND | ND | ND | 1.52 |
| | | 653 | (1) | ++++ | ++++ | ++++ | +++ | ND | 1.79 | ND | ND | ND | ND | ND |
| | | 655 | (1) | ++++ | ++++ | ++++ | ++ | ND | 1.62 | ND | ND | ND | ND | ND |
| ENTERITIDIS | D1 | 736 | (1) | +++ | ++++ | ++ | +++ | 1.67 | 1.83 | ND | ND | ND | ND | ND |
| | | 735 | (1) | ++++ | ++++ | +++ | +++ | ND | 1.34 | ND | ND | ND | ND | ND |
| | | 737 | (1) | ++++ | ++++ | ++ | +++ | ND | 1.66 | ND | ND | ND | ND | ND |
| | | 738 | (1) | ++++ | ++++ | ++ | +++ | ND | 1.00 | ND | ND | ND | ND | ND |
| HEIDELBERG | B | 626 | (1) | +++ | +++ | ++++ | ++ | 1.09 | 1.62 | ND | ND | ND | ND | ND |
| | | 627 | (1) | ++ | ++ | ++ | ++ | ND | 0.83 | ND | ND | ND | ND | ND |
| | | 625 | (1) | +++ | +++ | ++ | ++ | ND | 1.58 | ND | ND | ND | ND | ND |
| | | 628 | (1) | +++ | +++ | ++ | ++ | ND | 1.18 | ND | ND | ND | ND | ND |
| NEWPORT | C2 | 719 | (1) | +++ | +++ | ++++ | +++ | 1.04 | 1.58 | ND | ND | ND | ND | ND |
| | | 718 | (1) | ++++ | +++ | ++ | +++ | ND | 1.05 | ND | ND | ND | ND | ND |
| | | 717 | (1) | +++ | +++ | ++++ | ++++ | ND | 1.96 | ND | ND | ND | ND | ND |
| | | 721 | (1) | +++ | ++++ | ++++ | ++++ | ND | 1.60 | ND | ND | ND | ND | ND |
| | | 720 | (1) | +++ | ++++ | ++++ | ++++ | ND | 1.21 | ND | ND | ND | ND | ND |
| INFANTIS | C1 | 670 | (1) | ++++ | ++++ | ++++ | ++++ | 0.59 | 1.03 | ND | ND | 1.04 | 0.85 | ND |
| | | 671 | (1) | ++++ | ++++ | ++++ | +++ | ND | 1.53 | ND | ND | ND | ND | ND |
| | | 673 | (1) | ++++ | ++++ | ++++ | +++ | ND | 0.98 | ND | ND | ND | ND | ND |
| | | 672 | (1) | ++++ | ++++ | ++++ | ++++ | ND | 1.84 | ND | ND | ND | ND | ND |
| | | 675 | (1) | ND | ND | ND | ND | ND | 1.22 | ND | ND | ND | ND | ND |
| AGONA | B | 611 | (1) | +++ | +++ | ++++ | +++ | ND | ND | 2.10 | ND | 1.71 | 1.71 | ND |
| | | 610 | (1) | +++ | +++ | ++++ | ++++ | ND | 1.23 | ND | ND | ND | ND | ND |
| | | 612 | (1) | ++++ | +++ | ++++ | ++ | ND | 1.44 | ND | ND | ND | ND | ND |
| ST PAUL | B | 642 | (1) | ++++ | ++++ | ++++ | +++ | 1.60 | 1.50 | ND | ND | ND | ND | ND |
| | | 643 | (1) | +++ | +++ | ++++ | ++ | ND | 1.55 | ND | ND | ND | ND | ND |
| | | 641 | (1) | +++ | ++++ | ++++ | +++ | ND | 1.03 | ND | ND | ND | ND | ND |
| MONTEVIDEO | C1 | 678 | (1) | ++++ | +++ | − | ++++ | 1.55 | 1.83 | 1.67 | ND | 1.05 | 1.63 | ND |
| | | 679 | (1) | +++ | +++ | − | +++ | ND | 0.49 | ND | ND | ND | ND | ND |
| | | 680 | (1) | ++++ | ++++ | ++++ | ++++ | ND | 1.13 | ND | ND | ND | ND | ND |
| | | 681 | (1) | +++ | ++++ | +++ | ++++ | ND | 1.70 | ND | ND | ND | ND | ND |
| TYPHI | D1 | 754 | (1) | + | ++++ | − | ++++ | 0.14 | 1.16 | ND | ND | ND | ND | ND |
| | | 757 | (1) | + | +++ | − | ++++ | ND | 0.84 | ND | ND | ND | ND | ND |
| | | 755 | (1) | ++ | ++++ | − | ++++ | ND | 1.05 | ND | ND | ND | ND | 1.21 |
| | | 758 | (1) | + | ++++ | − | +++ | ND | 0.59 | ND | ND | ND | ND | ND |
| | | 756 | (1) | + | ++++ | − | +++ | ND | 2.37 | ND | ND | ND | ND | ND |
| | | 753 | (1) | +/−− | ++++ | − | +++ | ND | 0.92 | ND | ND | ND | ND | ND |
| | | 752 | (1) | + | ++++ | − | +++ | ND | 1.38 | ND | ND | ND | ND | ND |
| ORANIENBURG | C1 | 683 | (1) | +++ | ++++ | − | +++ | 1.41 | 1.66 | ND | ND | ND | ND | ND |
| | | 684 | (1) | +++ | ++++ | − | +++ | ND | 0.87 | ND | ND | ND | ND | ND |
| | | 686 | (1) | +++ | ++++ | − | +++ | ND | 1.53 | ND | ND | ND | ND | ND |
| | | 685 | (1) | +++ | ++++ | − | ++ | ND | 1.59 | ND | ND | ND | ND | ND |
| MUENCHEN | C2 | 712 | (1) | +++ | ++ | ++++ | +++ | 0.99 | 1.74 | ND | ND | 1.57 | ND | ND |
| | | 715 | (1) | + | + | +++ | ++ | ND | 1.05 | ND | ND | ND | ND | ND |
| | | 714 | (1) | +++ | +++ | ++++ | ++++ | ND | 1.47 | ND | ND | ND | ND | ND |
| | | 713 | (1) | +++ | ++++ | ++++ | ++++ | ND | 2.09 | 2.02 | ND | ND | ND | ND |
| JAVIANA | D1 | 741 | (1) | +++ | ++++ | ++++ | ++++ | 1.03 | 1.78 | ND | ND | ND | ND | ND |
| | | 742 | (1) | +++ | +++ | +++ | +++ | ND | 1.67 | ND | ND | ND | ND | ND |
| BLOCKLEY | C2 | 702 | (1) | +++ | ++++ | +++ | +++ | 1.17 | 1.76 | ND | ND | ND | ND | ND |
| | | 705 | (1) | ++ | ++ | +++ | +++ | ND | 1.09 | ND | ND | ND | ND | ND |
| | | 701 | (1) | ++++ | ++++ | +++ | ++++ | ND | 0.84 | ND | ND | ND | ND | ND |
| | | 703 | (1) | +++ | ++++ | +++ | ++++ | ND | 1.26 | ND | ND | ND | ND | ND |
| DERBY | B | 620 | (1) | ++++ | +++ | ++++ | ++++ | 0.67 | 1.28 | 2.10 | ND | 1.38 | 1.43 | ND |
| | | 621 | (1) | +++ | +++ | ++++ | ++ | ND | 1.55 | ND | ND | ND | ND | ND |
| | | 623 | (1) | +++ | +++ | ++++ | +++ | ND | 1.08 | ND | ND | ND | ND | ND |
| | | 622 | (1) | +++ | +++ | ++++ | ++ | ND | 0.76 | ND | ND | ND | ND | ND |
| THOMPSON | C1 | 695 | (1) | +++ | +++ | +++ | ++ | 0.90 | 1.42 | ND | ND | ND | ND | ND |
| | | 693 | (1) | +++ | +++ | +++ | +++ | ND | 1.26 | ND | ND | ND | ND | ND |
| | | 694 | (1) | +++ | +++ | +++ | +++ | ND | 0.53 | ND | ND | ND | ND | ND |
| | | 696 | (1) | +++ | +++ | +++ | +++ | ND | 0.56 | ND | ND | ND | ND | ND |
| | | 692 | (1) | +++ | +++ | +++ | +++ | ND | 1.63 | ND | ND | ND | ND | ND |
| ANATUM | E1 | 765 | (1) | ++++ | ++++ | ++++ | ++++ | 1.10 | 1.89 | 2.10 | ND | 1.76 | 1.51 | ND |
| | | 766 | (1) | ++++ | +++ | ++++ | ++++ | ND | 1.68 | ND | ND | ND | ND | ND |
| | | 763 | (1) | ++++ | +++ | ++++ | ++++ | ND | 1.62 | ND | ND | ND | ND | ND |
| | | 764 | (1) | ++++ | +++ | ++++ | ++++ | ND | 1.18 | ND | ND | ND | ND | ND |
| TYPHI-MURIUM (copenhagen) | B | 650 | (1) | ++++ | ++++ | − | +++ | 1.77 | 2.06 | ND | ND | ND | ND | ND |
| | | 648 | (1) | +++ | +++ | ++++ | ++ | ND | 0.36 | ND | ND | ND | ND | ND |
| | | 652 | (1) | ++++ | ++++ | ++++ | +++ | ND | 1.24 | ND | ND | ND | ND | ND |
| | | 651 | (1) | ++++ | ++++ | − | +++ | ND | 1.69 | ND | ND | ND | ND | ND |
| | | 647 | (1) | ++++ | ++++ | − | ++++ | ND | 1.88 | ND | ND | ND | ND | ND |
| | | 649 | (1) | ++++ | +++ | − | ++++ | ND | 1.63 | ND | ND | ND | ND | ND |
| PANAMA | D1 | 745 | (1) | +++ | +++ | − | ++ | 0.89 | 1.56 | ND | ND | ND | ND | ND |
| | | 746 | (1) | +++ | ++++ | − | ++++ | ND | ND | ND | ND | ND | ND | ND |

TABLE 2-continued

SALMONELLA INCLUSIVITY DATA

| SALMONELLA SEROVAR | TYPE | STRAIN | SOURCE | DOT BLOT HYBRIDIZATION PROBES | | | | LIQUID HYBRIDIZATION | | | | | | |
|---|---|---|---|---|---|---|---|---|---|---|---|---|---|---|
| | | | | 1165 | 1200 | 849 | 1166 | 1166/1165 | 1166/1200 | 1166/1165/1200 | 1166/849 | 1166/1165/1200/849 | 1166/1165/1166/1200/849 | 1069/1166/1200/849 |
| | | 747 | (1) | ++++ | ++++ | − | +++ | ND | 0.98 | ND | ND | ND | ND | ND |
| | | 748 | (1) | ++++ | ++++ | − | ++++ | ND | 1.28 | ND | ND | ND | ND | ND |
| BRAENDERUP | C1 | 660 | (1) | +++ | +++ | ++ | +++ | 1.09 | 1.80 | ND | ND | ND | ND | ND |
| | | 661 | (1) | +++ | +++ | ++ | ++ | ND | 1.27 | ND | ND | ND | ND | ND |
| | | 659 | (1) | ++++ | +++ | +++ | ++ | ND | 0.87 | ND | ND | ND | ND | ND |
| | | 662 | (1) | ++++ | ++++ | +++ | +++ | ND | ND | ND | ND | ND | ND | ND |
| HADAR | C2 | GT0623 | (2) | ND | ND | ND | ND | 0.89 | 1.79 | ND | ND | ND | ND | ND |
| SCHWARTZENGRUND | B | GT0546 | (2) | ND | ND | ND | ND | 1.15 | 1.91 | ND | ND | ND | ND | ND |
| JAVA | B | 629 | (1) | +++ | +++ | ++++ | +/− | 0.94 | 1.44 | ND | ND | ND | ND | ND |
| | | 631 | (1) | +++ | +++ | ++++ | +++ | ND | 1.11 | ND | ND | ND | ND | ND |
| | | 632 | (1) | ++++ | +++ | ++++ | +++ | ND | 0.94 | ND | ND | ND | ND | ND |
| LITCHFIELD | C2 | 710 | (1) | ++++ | ++++ | ++++ | ++++ | 1.76 | 1.95 | ND | ND | ND | ND | ND |
| BREDENEY | B | 615 | (1) | ++++ | +++ | − | ++ | 0.66 | 1.31 | ND | ND | ND | ND | ND |
| | | 617 | (1) | ++++ | +++ | − | ++++ | ND | 1.85 | ND | ND | ND | ND | ND |
| OHIO | C1 | 682 | (1) | ++ | +++ | ++++ | ++ | 0.66 | 1.35 | ND | ND | ND | ND | ND |
| MANHATTAN | C2 | GT0630 | (2) | ND | ND | ND | ND | 0.85 | 1.80 | ND | ND | ND | ND | ND |
| LONDON | E1 | 770 | (1) | +++ | +++ | − | + | 1.56 | 1.81 | ND | ND | ND | ND | ND |
| | | 769 | (1) | ++++ | ++++ | − | ++++ | ND | 1.59 | ND | ND | ND | ND | ND |
| MISSISSIPPI | G2 | 800 | (1) | ++++ | ++++ | − | +++ | 1.65 | 1.95 | ND | ND | ND | ND | ND |
| SENFTENBERG | E4 | 788 | (1) | ++++ | +++ | ++++ | +++ | 0.78 | 1.46 | 1.59 | ND | 1.40 | ND | ND |
| | | 789 | (1) | ++++ | +++ | ++++ | +++ | ND | 1.02 | ND | ND | ND | ND | ND |
| SAN DEIGO | B | 644 | (1) | + | ++ | ++++ | ++ | 0.33 | 1.40 | ND | ND | 1.01 | ND | ND |
| POONA | G1 | 795 | (1) | ++++ | +++ | − | ++++ | 0.88 | 1.78 | ND | ND | ND | ND | ND |
| | | 796 | (1) | ++++ | ++++ | − | ++++ | ND | 1.90 | ND | ND | ND | ND | ND |
| | | 797 | (1) | ++++ | ++++ | − | ++++ | ND | 1.64 | ND | ND | ND | ND | ND |
| DUBLIN | D1 | 733 | (1) | ++++ | ++++ | ++++ | ++++ | 1.66 | 1.75 | ND | ND | ND | ND | ND |
| BAREILLY | C1 | 657 | (1) | ++++ | ++++ | ++++ | +++ | 1.19 | 1.61 | ND | ND | ND | ND | ND |
| | | 658 | (1) | ++++ | ++++ | ++++ | ++ | ND | 1.83 | ND | ND | ND | ND | ND |
| WELTERVREDEN | G1 | GT911 | (1) | ND | ND | ND | ND | ND | 1.62 | 2.00 | ND | 1.78 | 1.8 | 1.8 |
| CERRO | K | 806 | (1) | ++++ | +++ | ++++ | ++++ | 1.69 | 1.95 | ND | ND | ND | ND | ND |
| | | 814 | (1) | ++++ | ++++ | +++ | +++ | ND | 1.64 | ND | ND | ND | ND | ND |
| | | 816 | (1) | ++++ | ++++ | +++ | ++++ | ND | 1.13 | ND | ND | ND | ND | ND |
| | | 815 | (1) | ++++ | ++++ | +++ | +++ | ND | 1.66 | ND | ND | ND | ND | ND |
| | | 817 | (1) | ++++ | ++++ | ++++ | ++++ | ND | 1.01 | ND | ND | ND | ND | ND |
| PARATYPHI | B | 605 | (1) | ++++ | +++ | +++ | + | 1.86 | 1.91 | ND | 0.98 | ND | ND | ND |
| | | 635 | (1) | +++ | + | ++++ | +++ | 0.34 | 0.18 | 0.39 | 0.60 | 0.91 | ND | 0.76 |
| | | 638 | (1) | +++ | ++ | ++++ | +++ | 1.77 | 0.97 | ND | 1.20 | ND | ND | ND |
| | | 633 | (1) | ++++ | +++ | ++++ | ++++ | 1.84 | 1.64 | ND | 1.29 | ND | ND | ND |
| | | 637 | (1) | ++ | +++ | ++++ | +++ | 1.90 | 1.79 | ND | 1.48 | ND | ND | ND |
| | | 636 | (1) | +++ | ++ | +++ | +++ | 1.20 | 1.25 | 2.09 | 0.21 | ND | ND | ND |
| | | 634 | (1) | ++++ | +++ | ++++ | +++ | ND | ND | ND | ND | ND | ND | ND |
| GIVE | E1 | 768 | (1) | +++ | ++++ | ++ | ++++ | 0.50 | 1.56 | ND | ND | ND | ND | ND |
| CHESTER | B | 619 | (1) | ++++ | +++ | ++++ | ++++ | 1.90 | 1.97 | ND | ND | ND | ND | ND |
| MBANDAKA | C1 | 675 | (1) | +++ | +++ | ++++ | +++ | 1.22 | 1.77 | 2.00 | ND | 1.89 | 1.86 | ND |
| MUENSTER | E1 | 772 | (1) | ++++ | +++ | ++++ | ++++ | 0.47 | 1.43 | 2.00 | ND | 1.79 | 1.67 | ND |
| | | 773 | (1) | ++++ | ++++ | ++++ | ++++ | ND | 1.57 | ND | ND | ND | ND | ND |
| READING | B | 640 | (1) | +++ | +++ | ++ | ++ | 0.36 | 1.12 | ND | ND | ND | ND | ND |
| | | 639 | (1) | +++ | +++ | ++++ | +++ | ND | 1.08 | ND | ND | ND | ND | ND |
| TENNESSEE | C1 | 690 | (1) | +++ | ++++ | +++ | ++ | 1.05 | 1.82 | ND | ND | ND | ND | ND |
| | | 691 | (1) | +++ | ++++ | ++++ | ++++ | ND | 1.17 | ND | ND | ND | ND | ND |
| HAARDT | C3 | 724 | (1) | +++ | ++ | +++ | ++++ | 1.60 | 1.86 | ND | ND | ND | ND | ND |
| | | 708 | (1) | +++ | +++ | +++ | ++++ | ND | 1.02 | ND | ND | ND | ND | ND |
| INDIANA | B | GT0628 | (2) | ND | ND | ND | ND | 1.10 | 1.42 | ND | ND | ND | ND | ND |
| HAVANA | G2 | 799 | (1) | +++ | +++ | ++++ | +++ | 1.04 | 1.61 | ND | ND | 1.60 | ND | ND |
| | | 360 | (5) | ND | ND | ND | ND | ND | ND | 1.92 | ND | ND | ND | ND |
| NORWICH | C1 | GT0627 | (2) | ND | ND | ND | ND | 0.60 | 1.25 | ND | ND | ND | ND | ND |
| BOVISMORBIFICANS | C2 | 704 | (1) | +++ | +++ | − | ++++ | 0.68 | 1.21 | 2.00 | ND | 1.22 | ND | ND |
| WORTHINGTON | G2 | 802 | (1) | +++ | +++ | +++ | +++ | 0.65 | 1.03 | ND | ND | ND | ND | ND |
| | | 803 | (1) | ++++ | ++++ | ++++ | ++++ | ND | 1.57 | ND | ND | ND | ND | ND |
| BERTA | D1 | 729 | (1) | +++ | +++ | ++++ | +++ | 1.23 | 1.43 | ND | ND | ND | ND | ND |
| PARATYPHI | A | 600 | (1) | ++++ | ++++ | ++++ | +++ | 0.52 | 0.88 | ND | ND | ND | ND | ND |
| | | 603 | (1) | +++ | ++ | ++++ | +++ | ND | 0.62 | ND | ND | ND | ND | ND |
| | | 601 | (1) | ++++ | +++ | ++++ | +++ | ND | 0.92 | ND | ND | ND | ND | ND |

TABLE 2-continued

SALMONELLA INCLUSIVITY DATA

| SALMON-ELLA SERO-VAR | TYPE | STRAIN | SOURCE | DOT BLOT HYBRIDIZATION PROBES | | | | LIQUID HYBRIDIZATION | | | | | | |
|---|---|---|---|---|---|---|---|---|---|---|---|---|---|---|
| | | | | 1165 | 1200 | 849 | 1166 | 1166 1165 | 1166 1200 | 1166 1165 1200 | 1166 1165 849 | 1166 1200 849 | 1166 1165 849 | 1069 1166 1200 849 |
| | | 602 | (1) | ++++ | +++ | ++++ | ++ | ND | 0.93 | ND | ND | ND | ND | ND |
| | | 604 | (1) | ++++ | +++ | ++++ | ++++ | ND | 0.97 | ND | ND | ND | ND | ND |
| VIR-CHOW | C1 | 698 | (1) | +++ | ++++ | − | ++++ | 0.82 | 1.49 | ND | ND | ND | ND | ND |
| | | 699 | (1) | ++++ | ++++ | +++ | ++++ | ND | 0.84 | ND | ND | ND | ND | ND |
| RUBI-SLAW | F | 792 | (1) | ++++ | +++ | − | ++++ | 1.02 | 1.72 | 1.70 | ND | ND | ND | ND |
| | | 793 | (1) | +++ | +++ | − | +++ | ND | 1.88 | ND | ND | ND | ND | ND |
| | | 535 | (5) | ND | ND | ND | ND | ND | ND | 1.88 | ND | ND | ND | ND |
| KOTTBUS | C2 | 709 | (1) | +++ | +++ | ++ | +++ | 1.39 | 1.81 | ND | ND | ND | ND | ND |
| ADE-LAIDE | O | 832 | (1) | ++++ | ++++ | − | +++ | 1.18 | 1.55 | ND | ND | ND | ND | ND |
| | | 833 | (1) | +++ | ++++ | − | + | ND | 0.78 | ND | ND | ND | ND | ND |
| JOHAN-NES-BURG | R | 846 | (1) | ++++ | ++++ | − | +++ | 0.89 | 1.57 | ND | ND | ND | ND | ND |
| BRAND-ENBURG | B | 614 | (1) | ++++ | +++ | ++++ | ++++ | 1.44 | 2.00 | ND | ND | ND | ND | ND |
| ALBANY | C3 | GT0662 | (3) | ND | ND | ND | ND | 0.62 | 1.62 | ND | ND | ND | ND | ND |
| ALA-CHOA | O | 834 | (1) | ++++ | ++++ | − | ++ | 1.38 | 1.85 | ND | ND | ND | ND | ND |
| HART-FORD | C1 | 669 | (1) | ++++ | +++ | ++++ | +++ | 0.80 | 1.70 | ND | ND | ND | ND | ND |
| KEN-TUCKY | C3 | 725 | (1) | ++ | +++ | ++++ | ++++ | 0.40 | 1.65 | ND | ND | ND | ND | ND |
| MIAMI | D1 | GT0620 | (3) | ND | ND | ND | ND | 1.10 | 1.86 | ND | ND | ND | ND | ND |
| LIVING-STONE | C1 | 674 | (1) | ++++ | ++ | ++++ | ++ | 0.78 | 1.42 | ND | ND | ND | ND | ND |
| MELEA-GRIDIS | E1 | 771 | (1) | ++++ | ++++ | ++++ | ++++ | 1.71 | 1.84 | 1.79 | ND | 1.42 | ND | ND |
| NEWING-TON | E2 | 778 | (1) | ++ | +++ | ++++ | ++++ | 1.49 | 1.87 | 1.88 | ND | ND | ND | ND |
| STANLEY | B | 646 | (1) | +++ | ++ | ++++ | ++ | 0.36 | 0.78 | ND | ND | ND | ND | ND |
| CHOLER-ASUIS | C1 | 663 | (1) | ++++ | ++++ | ++++ | +++ | 1.40 | 1.91 | ND | ND | ND | ND | ND |
| | | 665 | (1) | +++ | ++ | +++ | ++ | ND | 1.81 | ND | ND | ND | ND | ND |
| | | 668 | (1) | ++++ | +++ | ++++ | +++ | ND | 1.93 | ND | ND | ND | ND | ND |
| | | 666 | (1) | ++++ | +++ | ++++ | ++ | ND | 0.86 | ND | ND | ND | ND | ND |
| | | 667 | (1) | +++ | +++ | ++++ | + | ND | 1.59 | ND | ND | ND | ND | ND |
| GAMIN-ARA | I | 811 | (1) | +++ | +++ | − | +++ | 1.72 | 1.81 | ND | ND | ND | ND | ND |
| DRY-POOL | E2 | GT0621 | (3) | ND | ND | ND | ND | 1.80 | 1.86 | 1.85 | ND | 1.53 | ND | ND |
| OSLO | C1 | 687 | (1) | +++ | +++ | +++ | ++++ | 0.78 | 0.59 | ND | ND | ND | ND | ND |
| CUBANA | G2 | GT0661 | (2) | ND | ND | ND | ND | 1.26 | 1.82 | 1.80 | ND | 1.50 | ND | ND |
| DUES-SELDORF | C2 | 706 | (1) | +++ | ++++ | − | ++++ | 0.86 | 1.13 | ND | ND | ND | ND | ND |
| MINNE-SOTA | L | 818 | (1) | ++++ | ++++ | +++ | ++++ | 1.19 | 1.78 | ND | ND | ND | ND | ND |
| | | 819 | (1) | +/− | − | ++ | − | ND | ND | ND | 1.57 | ND | 1.64 | |
| CALI-FORNIA | B | GT0625 | (2) | ND | ND | ND | ND | 1.62 | 1.76 | ND | ND | ND | ND | ND |
| SAPHRA | I | | | ND | ND | ND | ND | ND | 1.82 | ND | ND | ND | ND | ND |
| NEW-BRUNS-WICK | E2 | 782 | (1) | ++++ | ++++ | − | ++++ | 1.32 | 1.52 | 1.94 | ND | 1.35 | ND | ND |
| | | 783 | (1) | ++++ | +++ | +++ | +++ | ND | 1.04 | ND | ND | ND | ND | ND |
| | | 784 | (1) | ++++ | ++++ | +++ | ++++ | ND | 1.37 | ND | ND | ND | ND | ND |
| UGANDA | E1 | GT0626 | (2) | ND | ND | ND | ND | 1.35 | 1.59 | ND | ND | ND | ND | ND |
| ARI-ZONAE | | 910 | (1) | ++ | +++ | − | ++ | 0.23 | 1.15 | ND | ND | ND | ND | ND |
| | | 925 | (1) | ++++ | ++++ | ++++ | +++ | 0.06 | 0.44 | ND | ND | ND | ND | ND |
| | | 939 | (1) | ++ | +++ | − | +++ | 0.45 | 0.76 | 0.54 | ND | ND | ND | ND |
| | | 902 | (1) | ++++ | +++ | − | ++ | ND | 1.44 | ND | ND | ND | ND | ND |
| | | 904 | (1) | ++++ | +++ | − | ++ | ND | 1.35 | ND | ND | ND | ND | ND |
| | | 911 | (1) | + | +++ | − | ++ | ND | 1.08 | ND | ND | ND | ND | ND |
| | | 917 | (1) | +++ | +++ | − | +++ | ND | 1.76 | ND | ND | ND | ND | ND |
| | | 921 | (1) | +++ | ++ | ++ | ++ | ND | 0.73 | ND | ND | ND | ND | ND |
| | | 930 | (1) | +++ | +++ | ++ | +++ | ND | 0.63 | ND | ND | ND | ND | ND |
| | | 941 | (1) | − | + | − | − | ND | 0.56 | ND | ND | 0.33 | ND | ND |
| | | 907 | (1) | ++++ | ++++ | − | +++ | ND | 1.28 | ND | ND | ND | ND | ND |
| | | 908 | (1) | ++++ | ++++ | − | +++ | ND | 1.12 | ND | ND | ND | ND | ND |
| | | 906 | (1) | ++++ | ++++ | − | ++ | ND | 1.12 | ND | ND | ND | ND | ND |
| | | 903 | (1) | ++++ | ++++ | − | ++++ | ND | 0.74 | ND | ND | ND | ND | ND |
| | | 905 | (1) | ++++ | ++++ | − | +++ | ND | 0.64 | ND | ND | ND | ND | ND |
| | | 924 | (1) | ++++ | ++++ | ++++ | +++ | ND | 1.66 | ND | ND | ND | ND | ND |
| | | 927 | (1) | +++ | ++++ | − | +++ | ND | 1.50 | ND | ND | ND | ND | ND |
| | | 926 | (1) | ++++ | ++++ | ++++ | ++ | ND | 0.73 | ND | ND | ND | ND | ND |
| | | 929 | (1) | ++++ | ++++ | − | ++ | ND | 0.84 | ND | ND | ND | ND | ND |
| | | 928 | (1) | ++++ | ++++ | − | ++ | ND | 1.06 | ND | ND | ND | ND | ND |
| | | 923 | (1) | +++ | ++++ | − | ++ | ND | 0.99 | ND | ND | ND | ND | ND |
| | | 909 | (1) | ++++ | ++++ | − | +++ | ND | 0.61 | ND | ND | ND | ND | ND |

TABLE 2-continued

SALMONELLA INCLUSIVITY DATA

| SALMON-ELLA SEROVAR | TYPE | STRAIN | SOURCE | DOT BLOT HYBRIDIZATION PROBES | | | | LIQUID HYBRIDIZATION | | | | | | |
|---|---|---|---|---|---|---|---|---|---|---|---|---|---|---|
| | | | | 1165 | 1200 | 849 | 1166 | 1166 / 1165 | 1166 / 1200 | 1166 1165 / 1200 | 1166 / 849 | 1166 1200 / 849 | 1166 1165 / 1200 849 | 1069 1166 1200 / 849 |
| | | 918 | (1) | ++++ | ++++ | − | ++ | ND | 0.64 | ND | ND | ND | ND | ND |
| | | 912 | (1) | ++++ | ++++ | − | +++ | ND | 1.63 | ND | ND | ND | ND | ND |
| | | 915 | (1) | ++ | ++++ | − | ++ | ND | 1.43 | ND | ND | ND | ND | ND |
| | | 913 | (1) | + | ++++ | − | + | ND | 1.59 | ND | ND | ND | ND | ND |
| | | 914 | (1) | +++ | ++++ | − | +/− | ND | 1.44 | ND | ND | ND | ND | ND |
| | | 916 | (1) | ++++ | ++++ | − | +++ | ND | 0.75 | ND | ND | ND | ND | ND |
| | | 938 | (1) | +++ | ++++ | − | ++ | ND | 1.01 | ND | ND | ND | ND | ND |
| | | 937 | (1) | ++ | ++++ | − | +++ | ND | 0.49 | ND | ND | ND | ND | ND |
| | | 920 | (1) | ++++ | ++++ | +++ | ++++ | ND | 1.46 | ND | ND | ND | ND | ND |
| ARIZONAE | | 940 | (1) | ++ | ++++ | − | +++ | ND | 1.63 | ND | ND | 1.81 | ND | ND |
| | | 922 | (1) | ++++ | ++++ | +++ | ++ | ND | 1.18 | ND | ND | ND | ND | ND |
| | | 919 | (1) | ++++ | ++++ | +++ | +++ | ND | 1.21 | ND | ND | ND | ND | ND |
| | | 933 | (1) | ++++ | +++ | − | +++ | ND | 1.57 | ND | ND | ND | ND | ND |
| | | 934 | (1) | ++++ | ++++ | − | ++ | ND | 0.51 | ND | ND | ND | ND | ND |
| | | 931 | (1) | +++ | ++++ | − | +++ | ND | 1.60 | ND | ND | ND | ND | ND |
| | | 932 | (1) | +++ | ++++ | ++++ | +++ | ND | 1.67 | ND | ND | ND | ND | ND |
| | | 935 | (1) | + | ++++ | − | +++ | ND | ND | ND | ND | ND | ND | ND |
| | | 936 | (1) | − | + | ++++ | +/− | ND | ND | ND | ND | ND | ND | ND |
| | | 942 | (1) | ++ | +++ | − | +++ | ND | ND | ND | ND | ND | ND | ND |
| URBANA | B | 829 | (1) | ++++ | ++++ | − | ++++ | 0.31 | 0.79 | 0.81 | ND | ND | ND | ND |
| | | 830 | (1) | ++++ | ++++ | − | ++++ | ND | 1.89 | ND | ND | ND | ND | ND |
| LINDENBURG | C2 | GT0910 | (1) | ND | ND | ND | ND | ND | 1.10 | ND | ND | ND | ND | ND |
| | | 0951 | (4) | ND | ND | ND | ND | ND | ND | 1.75 | ND | ND | ND | ND |
| KINSHASA | E2 | GT0908 | (1) | ND | ND | ND | ND | ND | 1.18 | ND | ND | ND | ND | ND |
| STANLEYVILLE | B | GT0909 | (1) | ND | ND | ND | ND | ND | 1.39 | ND | ND | ND | ND | ND |
| IVERNESS | P | 839 | (1) | +++ | ++++ | − | +++ | 1.346 | 1.79 | ND | ND | ND | ND | ND |
| | | 840 | (1) | ++++ | +++ | ++++ | ++++ | ND | 1.38 | ND | ND | ND | ND | ND |
| NIENSTADTEN | C4 | GT0629 | (2) | ND | ND | ND | ND | 1.14 | 1.31 | ND | ND | ND | ND | ND |
| EASTBORNE | D1 | 734 | (1) | +++ | ++++ | +++ | +++ | 0.51 | 1.12 | ND | ND | ND | ND | ND |
| PENSACOLA | D1 | 749 | (1) | ++++ | +++ | ++++ | +++ | 1.04 | 1.73 | 1.79 | ND | ND | ND | ND |
| ABERDEEN | F | 791 | (1) | ++++ | +++ | +++ | ++++ | 1.28 | 1.90 | 1.95 | ND | ND | ND | ND |
| POMONA | M | 823 | (1) | ++++ | ++++ | − | ++++ | 0.99 | 1.88 | 1.88 | ND | ND | ND | ND |
| THOMASVILLE | E3 | GT0615 | (3) | ND | ND | ND | ND | 1.48 | 1.77 | ND | ND | ND | ND | ND |
| SINGAPORE | C1 | GT0622 | (3) | ND | ND | ND | ND | 1.07 | 1.65 | ND | ND | ND | ND | ND |
| IBADEN | G1 | GT0912 | (1) | ND | ND | ND | ND | ND | 1.22 | ND | ND | ND | ND | ND |
| KREFELD | E4 | 786 | (1) | −−/+ | − | ++++ | − | 0.85 | 1.25 | 1.59 | ND | 1.32 | ND | 1.79 |
| LILLE | C1 | GT0618 | (3) | ND | ND | ND | ND | 1.68 | 1.50 | ND | ND | ND | ND | ND |
| MADELIA | H | GT0616 | (3) | ND | ND | ND | ND | 0.48 | 1.64 | ND | ND | ND | ND | ND |
| GLOSTRUP | C2 | 707 | (1) | ++++ | +++ | − | ++++ | 1.67 | 1.44 | 1.89 | ND | ND | ND | ND |
| BINZA | E2 | GT0619 | (3) | ND | ND | ND | ND | 1.35 | 1.31 | ND | ND | ND | ND | ND |
| LOMITA | C1 | GT0617 | (3) | ND | ND | ND | ND | 1.14 | 1.69 | ND | ND | ND | ND | ND |
| POTSDAM | C1 | STK43 | (2) | ND | ND | ND | ND | 1.60 | 1.28 | ND | ND | ND | ND | ND |
| CARRAU | H | 805 | (1) | +++ | +++ | − | +++ | 0.88 | 0.75 | 1.32 | ND | ND | ND | ND |
| HVITTINGFOSS | I | GT0913 | (1) | ND | ND | ND | ND | ND | 1.38 | ND | ND | ND | ND | ND |
| | | GT0950 | (4) | ND | ND | ND | ND | ND | 0.49 | ND | ND | ND | ND | ND |
| BULAWAYO | R | 845 | (1) | − | + | ++++ | +++ | 0.07 | 0.38 | 0.93 | ND | 1.06 | ND | ND |
| STRASSBOURG | D2 | 761 | (1) | +++ | +++ | ++ | +++ | ND | ND | 1.86 | 0.35 | 1.71 | ND | ND |
| FREETOWN | P | 838 | (1) | +++ | ++++ | − | +++ | ND | ND | 1.67 | 0.04 | 1.13 | ND | ND |
| BERN | R | 844 | (1) | + | + | − | + | ND | ND | 0.50 | 0.04 | 0.17 | ND | 0.2 |
| WASSENAAR | Z | 874 | (1) | +++ | +++ | − | ++ | ND | ND | 0.94 | 0.04 | 0.43 | ND | 0.96 |
| | | 873 | (1) | + | + | − | +/− | ND | ND | 0.83 | 0.06 | 0.30 | ND | 0.62 |
| FLINT | Z | 870 | (1) | +++ | + | − | ++++ | ND | ND | 1.84 | ND | 0.16* | ND | 0.02 |
| ILLINOIS | E3 | 779 | (1) | ++ | +++ | ++++ | ++ | ND | ND | 0.91 | ND | ND | ND | ND |
| | | 780 | (1) | +++ | +++ | ++++ | ++++ | ND | ND | 1.94 | ND | ND | ND | ND |
| AMERSFOORT | C1 | 656 | (1) | ++++ | ++++ | ++++ | ++ | ND | ND | 1.35 | ND | ND | ND | ND |
| BISPEG- | B | 613 | (1) | +++ | ++ | +++ | +++ | ND | ND | 1.04 | ND | ND | ND | ND |

TABLE 2-continued

SALMONELLA INCLUSIVITY DATA

| SALMON-ELLA SERO-VAR | TYPE | STRAIN | SOURCE | DOT BLOT HYBRIDIZATION PROBES | | | | LIQUID HYBRIDIZATION | | | | | | |
|---|---|---|---|---|---|---|---|---|---|---|---|---|---|---|
| | | | | 1165 | 1200 | 849 | 1166 | 1166 1165 | 1166 1200 | 1166 1165 1200 | 1166 849 | 1166 1165 1200 849 | 1166 1165 1200 849 | 1069 1166 1200 849 |
| JERG RIO-GRANDE | R | 848 | (1) | +++ | ++ | ++++ | +++ | ND | ND | 0.44 | ND | ND | ND | ND |
| BUNNIK (MONO) | U | 854 | (1) | ++++ | ++++ | ++++ | +++ | ND | ND | 1.65 | ND | ND | ND | ND |
| | | 855 | (1) | ++++ | ++++ | ++++ | ++++ | ND | ND | 1.98 | ND | ND | ND | ND |
| WAY-CROSS | R | 850 | (1) | ++++ | ++++ | ++ | ++++ | ND | ND | 0.95 | ND | ND | ND | ND |
| KING-ABWA | U | 856 | (1) | ++++ | ++++ | ++++ | ++++ | ND | ND | 1.59 | ND | ND | ND | ND |
| | | 857 | (1) | ++++ | ++++ | ++++ | ++++ | ND | ND | 1.85 | ND | ND | ND | ND |
| WES-LACO | T | 851 | (1) | ++ | ++ | ++++ | +++ | ND | ND | 1.35 | ND | ND | ND | ND |
| | | 852 | (1) | ++ | ++ | ++++ | ++ | ND | ND | 0.35 | ND | ND | ND | ND |
| NIAREM-BE | V | 859 | (1) | +++ | +++ | ++++ | +++ | ND | ND | 1.24 | ND | ND | ND | ND |
| CHAM-PAIGN | Q | 843 | (1) | ++++ | +++ | ++ | +++ | ND | ND | 1.86 | ND | ND | ND | ND |
| | | 842 | (1) | ++++ | ++++ | ++ | ++++ | ND | ND | 1.82 | ND | ND | ND | ND |
| GUINEA | V | 858 | (1) | +++ | +++ | ++++ | +++ | ND | ND | 1.91 | ND | ND | ND | ND |
| EMMA-STAD | P | 837 | (1) | ++++ | ++++ | ++++ | +++ | ND | ND | 1.78 | ND | ND | ND | ND |
| BERK-ELEY | U | 853 | (1) | +++ | +++ | +++ | ++ | ND | ND | 1.24 | ND | ND | ND | ND |
| ARKAN-SAS | E3 | 777 | (1) | ++++ | ++++ | ++++ | ++++ | ND | ND | 1.30 | ND | ND | ND | ND |
| UCCLE | 54 | 878 | (1) | +++ | +++ | +++ | +++ | ND | ND | 1.88 | ND | ND | ND | ND |
| HUMBER | 53 | 877 | (1) | ++ | +++ | ++++ | ++++ | ND | ND | 1.83 | ND | ND | ND | ND |
| BASEL | 58 | 883 | (1) | + | ++ | +++ | + | ND | ND | 1.98 | 0.96 | 1.53 | ND | ND |
| TOKAI | 57 | 882 | (1) | ++ | +++ | − | ++++ | ND | ND | 0.76 | ND | ND | ND | ND |
| TRE-FOREST | 51 | 875 | (1) | +++ | +++ | − | +++ | ND | ND | 1.92 | ND | ND | ND | ND |
| ARTIS | 56 | 880 | (1) | +++ | +++ | ++++ | ++++ | ND | ND | 1.68 | ND | ND | ND | ND |
| DAHLEM | Y | 867 | (1) | + | ++++ | +++ | ++ | ND | ND | 1.85 | ND | ND | ND | ND |
| UT-RECHT | 52 | 876 | (1) | ++++ | +++ | − | ++++ | ND | ND | 1.81 | ND | ND | ND | ND |
| QUIM-BAMBA | X | 865 | (1) | +++ | ++++ | +++ | +++ | ND | ND | 1.06 | ND | ND | ND | ND |
| HOR-SHAM | H | 809 | (1) | ++++ | ++++ | − | +++ | ND | ND | 1.95 | ND | ND | ND | ND |
| ONDER-STE-POORT | H | 807 | (1) | ++++ | ++++ | − | +++ | ND | ND | 1.90 | ND | ND | ND | ND |
| FLORIDA | H | 808 | (1) | ++++ | ++++ | − | +++ | ND | ND | 1.94 | ND | ND | ND | ND |
| BERGEN | X | 863 | (1) | ++++ | ++++ | +++ | +++ | ND | ND | 1.64 | ND | ND | ND | ND |
| QUINHON | X | 866 | (1) | + | +++ | − | ++ | ND | ND | 0.97 | ND | ND | ND | ND |
| GREEN-SIDE | Z | 871 | (1) | + | ++++ | +++ | ++ | ND | ND | 1.59 | ND | ND | ND | ND |
| DEVER-SOIR | W | 860 | (1) | ++++ | ++++ | − | +++ | ND | ND | 0.71 | ND | ND | ND | ND |
| LUCIANA | F | 787 | (1) | ++++ | +++ | − | ++++ | ND | ND | 1.90 | ND | ND | ND | ND |
| SP CDC STK 433 | G | 798 | (1) | ++++ | +++ | − | +++ | ND | ND | 1.93 | ND | ND | ND | ND |
| ORION | E1 | 775 | (1) | +++ | +++ | ++++ | ++++ | ND | ND | 1.82 | ND | ND | ND | ND |
| BLEG-DAM | D1 | 730 | (1) | +++ | ++ | ++++ | ++ | ND | ND | 1.64 | ND | ND | ND | ND |
| WESTER-STEDE | E4 | 790 | (1) | ++++ | ++++ | +++ | ++++ | ND | ND | 1.98 | ND | ND | ND | ND |
| DARES-SALAAM | D1 | 731 | (1) | +/−− | ++ | ++++ | ++ | ND | ND | 1.88* | 1.12* | 0.12 | ND | 0.36 |
| EAST-BOURNE | D1 | 734 | (1) | ++++ | ++++ | +++ | +++ | ND | ND | 1.67 | ND | ND | ND | ND |
| MOSCOW | D1 | 743 | (1) | ++ | +++ | ++++ | +++ | ND | ND | 1.91 | ND | ND | ND | ND |
| SP CDC STK 1218 | 64 | 886 | (1) | +/− | +++ | +++ | +++ | ND | ND | 1.68 | ND | ND | ND | ND |
| NAPOLI | D1 | 744 | (1) | +++ | +++ | ++++ | +++ | ND | ND | 1.99 | ND | ND | ND | ND |
| ROSTOCK | D1 | 750 | (1) | ++++ | ++++ | ++++ | +++ | ND | ND | 1.82 | ND | ND | ND | ND |
| SENDAI | D1 | 751 | (1) | ++++ | ++++ | ++++ | +++ | ND | ND | 1.98 | ND | ND | ND | ND |
| GATES-HEAD | D2 | 760 | (1) | ++++ | +++ | ++++ | ++++ | ND | ND | 1.92 | ND | ND | ND | ND |
| SP CDC STK 572 | E1 | 762 | (1) | +++ | +++ | ++++ | +++ | ND | ND | 1.90 | ND | ND | ND | ND |
| BUTAN-TAN | E1 | 767 | (1) | ++++ | ++++ | ++++ | ++++ | ND | ND | 1.93 | ND | ND | ND | ND |
| BROOK-FIELD | 66 | 888 | (1) | + | +++ | ++++ | ++ | ND | ND | 0.16 | 1.92* | ND | ND | 0.53 |
| | | 890 | (1) | +/− | − | ++++ | ++++ | ND | ND | 0.00 | 0.00 | 0.75** | ND | 1.09 |
| LUTON | 60 | 885 | (1) | ++++ | +++ | ++++ | ++++ | ND | ND | 1.86 | ND | ND | ND | ND |
| MON- | O | 835 | (1) | ++++ | ++++ | ++++ | +++ | ND | ND | 1.96 | ND | ND | ND | ND |

TABLE 2-continued
SALMONELLA INCLUSIVITY DATA

| SALMONELLA SEROVAR | TYPE | STRAIN | SOURCE | DOT BLOT HYBRIDIZATION PROBES | | | | LIQUID HYBRIDIZATION | | | | | | |
|---|---|---|---|---|---|---|---|---|---|---|---|---|---|---|
| | | | | 1165 | 1200 | 849 | 1166 | 1166 1165 | 1166 1200 | 1166 1165 1200 | 1166 849 | 1166 1200 849 | 1166 1165 1200 849 | 1069 1166 1200 849 |
| SHAUI | | 837 | (1) | ++++ | ++++ | − | +++ | ND | ND | 1.99 | ND | ND | ND | ND |
| FRESNO | D2 | 759 | (1) | +++ | +++ | − | +++ | ND | ND | 2.00 | ND | ND | ND | ND |
| RAMAT-GAN | N | 826 | (1) | ++++ | ++++ | − | ++++ | ND | ND | 1.77 | ND | ND | ND | ND |
| WAYNE | N | 831 | (1) | +++ | + | ++++ | +++ | ND | ND | 0.11 | 1.98* | 1.65 | ND | ND |
| STERN-SCHANTZE | N | 828 | (1) | +++ | +++ | +++ | ++ | ND | ND | 1.87 | ND | ND | ND | ND |
| SOERENGE | N | 827 | (1) | +++ | ++++ | +++ | +++ | ND | ND | 1.77 | ND | ND | ND | ND |
| NYBORG | E1 | 774 | (1) | +++ | +++ | − | +++ | ND | ND | 1.96 | ND | ND | ND | ND |
| MOREHEAD | N | 825 | (1) | ++ | +++ | − | ++++ | ND | ND | 1.60 | ND | ND | ND | ND |
| MATOPENI | N | 824 | (1) | ++++ | ++++ | ++++ | ++++ | ND | ND | 1.54 | ND | ND | ND | ND |
| PARATYPHI E. AF | C | 688 | (1) | ++++ | ++++ | ++++ | ++++ | ND | ND | 1.96 | ND | ND | ND | ND |
| NIKAWASIMA | C1 | 677 | (1) | ++++ | +++ | +++ | +/− | ND | ND | 1.85 | ND | ND | ND | ND |
| | | 676 | (1) | ++++ | +++ | − | ++ | ND | ND | 1.89 | ND | ND | ND | ND |
| SP CDC STK 219 | M | 820 | (1) | +++ | +++ | − | ++ | ND | ND | 1.76 | ND | ND | ND | ND |
| BABELSBERG | M | 821 | (1) | ++++ | ++++ | +++ | +++ | ND | ND | 1.94 | ND | ND | ND | ND |
| MBANDAKA | C1 | 711 | (1) | +++ | ++++ | +++ | +++ | ND | ND | 1.90 | ND | ND | ND | ND |
| NARASHINO | C2 | 716 | (1) | +++ | ++ | +++ | ++++ | ND | ND | 1.72 | ND | ND | ND | ND |
| TULEAR PHASE 2 | C2 | 723 | (1) | +/−− | ++ | +++ | ++ | ND | ND | 1.16 | ND | ND | ND | ND |
| VIRGINIA | C3 | 726 | (1) | +++ | ++ | ++++ | ++++ | ND | ND | 1.65 | ND | ND | ND | ND |
| TALLAHASSEE | C2 | 722 | (1) | +++ | +++ | +++ | ++++ | ND | ND | 1.94 | ND | ND | ND | ND |
| CDC 370-85 ENTERIC GP | | IG3252 | (1) | ++++ | ++++ | − | +++ | ND | ND | 1.75 | ND | ND | ND | ND |
| CDC 1018 2083-62 | VI | IG3251 | (1) | + | − | ++ | +++ | ND | ND | 0.78 | ND | 0.4 | ND | ND |
| TRANOROA | 55 | 879 | (1) | ++ | +++ | − | +++ | ND | ND | 1.92 | ND | ND | ND | ND |
| DAKAR | M | 822 | (1) | ++++ | ++++ | − | ++++ | ND | ND | 1.99 | ND | ND | ND | ND |
| RUTGERS | E1 | 897 | (1) | ++++ | +++ | − | ++++ | ND | ND | 2.01 | ND | ND | ND | ND |
| KARAMOJA | R | 847 | (1) | +++ | +++ | ++++ | +++ | ND | ND | 2.01 | ND | ND | ND | ND |
| SUNDSUALL | H | 810 | (1) | ++++ | ++++ | ++++ | +++ | ND | ND | 2.00 | ND | ND | ND | ND |
| NOTTINGHAM | I | 812 | (1) | ++++ | +++ | − | +++ | ND | ND | 1.95 | ND | ND | ND | ND |
| CHITTAGONG | E4 | 785 | (1) | +++ | +++ | + | ++++ | ND | ND | 1.81 | ND | ND | ND | ND |
| SCHLEISSHEIM | B | 645 | (1) | ++++ | +++ | +++ | ++ | ND | ND | 1.98 | ND | ND | ND | ND |
| ABORTUS EQUI | B | 607 | (1) | ++++ | +++ | ++++ | ++++ | ND | ND | 1.82 | ND | ND | ND | ND |
| ABORTUS OVIS | B | 609 | (1) | ++ | ++ | ++++ | ++ | ND | ND | 1.90 | ND | ND | ND | ND |
| | | 608 | (1) | ++++ | +++ | − | + | ND | ND | 1.67 | ND | ND | ND | ND |
| PULLORUM | E1 | 776 | (1) | ++++ | +++ | ++++ | +++ | ND | ND | 1.26 | ND | ND | ND | ND |
| KIRKEE | J | 813 | (1) | ++++ | ++++ | ++++ | ++++ | ND | ND | 1.98 | ND | ND | ND | ND |
| DUGBE | W | 861 | (1) | +++ | +++ | +++ | +++ | ND | ND | 1.97 | ND | ND | ND | ND |
| KAOLACK | X | 864 | (1) | ++++ | ++++ | − | +++ | ND | ND | 1.98 | ND | ND | ND | ND |
| CDC 1989 347-78 | VI | IG3245 | (1) | ++++ | + | ++++ | +++ | ND | ND | 1.90 | ND | 1.39 | ND | ND |
| CDC 1656 2131-71 | VI | IG3250 | (1) | ++++ | ++++ | +++ | +++ | ND | ND | 1.87 | ND | ND | ND | ND |
| COOK PHASE 1 | | 899 | (1) | ++++ | +++ | ++++ | +++ | ND | ND | 1.99 | ND | ND | ND | ND |
| KUNZENDORF | | 901 | (1) | ++++ | +++ | ++++ | +++ | ND | ND | 1.95 | ND | ND | ND | ND |
| ANARC- | | 900 | (1) | ++++ | +++ | ++ | +++ | ND | ND | 1.90 | ND | ND | ND | ND |

TABLE 2-continued
SALMONELLA INCLUSIVITY DATA

| SALMONELLA SEROVAR TICA | TYPE | STRAIN | SOURCE | DOT BLOT HYBRIDIZATION PROBES | | | | LIQUID HYBRIDIZATION | | | | | | |
|---|---|---|---|---|---|---|---|---|---|---|---|---|---|---|
| | | | | 1165 | 1200 | 849 | 1166 | 1166 1165 | 1166 1200 | 1166 1165 1200 | 1166 849 | 1166 1200 849 | 1166 1165 1200 849 | 1069 1166 1200 849 |
| CROSSNESS | 67 | 889 | (1) | +++ | +++ | +++ | ++++ | ND | ND | 1.92 | ND | ND | ND | ND |
| SP CDC STK NS3 2060 | 66 | 893 | (1) | − | − | +++ | ++ | ND | ND | 0.00 | 1.92* | 0.54 | ND | 0.86 |
| BONGOR | | 892 | (1) | − | − | +++ | + | ND | ND | 0.00 | 1.92* | 0.88* | ND | 0.28 |
| SP CDC STK N55 1925 | | 891 | (1) | − | − | ++++ | ++ | ND | ND | 0.00 | 1.81* | 1.79* | ND | 0.35 |
| SIMSBURY | H | 896 | (1) | +++ | ++ | +++ | ++++ | ND | ND | 2.04 | ND | ND | ND | ND |
| SP (CDC STK NS2 1957 2702-77) | | 895 | (1) | − | − | ++++ | ++++ | ND | ND | 0.00 | 1.87* | 0.22 | ND | 1.02 |
| SP (CDC STK NS2 1975 2703-76) | | 894 | (1) | − | − | +++ | + | ND | ND | 0.00 | 1.88* | 0.61 | ND | 1.46 |
| ESSEN | B | 624 | (1) | ++++ | +++ | ++++ | ++++ | ND | ND | 1.90 | 1.89* | ND | ND | ND |
| BETIOKY | 59 | 884 | (1) | ++++ | +++ | − | +++ | ND | ND | 1.95 | ND | ND | ND | ND |
| SPRINGS | R | 849 | (1) | + | +++ | ++++ | +++ | ND | ND | 1.90 | ND | ND | ND | ND |
| KUZENDORF | | 664 | (1) | ++++ | +++ | ++++ | +++ | ND | ND | 0.93 | ND | ND | ND | ND |
| TYPHISUIS | C1 | 697 | (1) | ++++ | ++++ | ++++ | ++++ | ND | ND | 1.56 | ND | ND | ND | ND |
| BORNUM | C4 | 727 | (1) | + | + | +++ | +/− | ND | ND | 1.36* | ND | 1.74 | ND | ND |
| HOOGRAVEN | Z | 872 | (1) | +/− | ++++ | − | +++ | ND | ND | 1.87 | ND | ND | ND | ND |
| LANSING | P | 841 | (1) | ++++ | +++ | ++++ | ++++ | ND | ND | 1.93 | ND | ND | ND | ND |
| CDC 1925 235-77 | V | IG3242 | (1) | − | − | ++++ | +++ | ND | ND | 0.00 | ND | 0.49 | ND | 0.92 |
| DCD 2229 232-84 | VI | IG3243 | (1) | ++++ | ++ | ++++ | +++ | ND | ND | 1.60 | ND | ND | ND | ND |
| CDC 1937 973-77 | VI | IG3244 | (1) | ++++ | ++++ | +++ | ++++ | ND | ND | 1.50 | ND | ND | ND | ND |
| CDC 1415 4603-68 | VI | IG3247 | (1) | ++++ | ++++ | ++++ | +++ | ND | ND | 1.53 | ND | ND | ND | ND |
| CDC 811 1411-60 | VI | IG3248 | (1) | +++ | ++ | ++++ | ++++ | ND | ND | 0.81 | ND | ND | ND | 1.06 |
| CDC 2269 1308-83 | V | IG3246 | (1) | − | − | ++ | +/− | ND | ND | 0.00 | 1.66* | ND | ND | 0.28 |
| BUDAPEST | B | 618 | (1) | +++ | ++ | ++++ | ++++ | ND | ND | 1.91 | ND | ND | ND | ND |
| BERE | X | 862 | (1) | +++ | +++ | +++ | +++ | ND | ND | 1.85 | ND | ND | ND | ND |
| DJAKARTA | Y | 868 | (1) | ++++ | +++ | − | +++ | ND | ND | 1.89 | ND | ND | ND | ND |
| BOECKER | H | 804 | (1) | ++++ | ++++ | − | ++++ | ND | ND | 1.91 | ND | ND | ND | ND |
| WITCHITA PHASE 2 | G2 | 801 | (1) | ++++ | ++++ | ++++ | ++++ | ND | ND | 1.87 | ND | ND | ND | ND |
| MARSHALL | G1 | 794 | (1) | ++++ | +++ | − | ++++ | ND | ND | 1.21 | ND | ND | ND | ND |
| MINNEAPOLIS | E3 | 781 | (1) | ++++ | ++++ | ++++ | +++ | ND | ND | 1.03 | ND | ND | ND | ND |
| AESCH | C2 | 898 | (1) | ++++ | +++ | +++ | ++++ | ND | ND | 0.85 | ND | ND | ND | ND |
| AMSTERDAM | E1 | SLR0392 | (5) | ND | ND | ND | ND | ND | ND | 1.88 | ND | ND | ND | ND |
| ABAE- | F | SLR0156 | (5) | ND | ND | ND | ND | ND | ND | 1.83 | ND | ND | ND | ND |

TABLE 2-continued

SALMONELLA INCLUSIVITY DATA

| SALMONELLA SEROVAR | TYPE STRAIN | SOURCE | DOT BLOT HYBRIDIZATION PROBES 1165 | 1200 | 849 | 1166 | LIQUID HYBRIDIZATION 1166 1165 | 1166 1200 | 1166 1165 1200 | 1166 1166 849 | 1166 1200 849 | 1166 1165 1200 849 | 1069 1166 1200 849 |
|---|---|---|---|---|---|---|---|---|---|---|---|---|---|
| TUBA | | | | | | | | | | | | | |

CODE:
++++ = POSITIVE CONTROL LEVEL OF HYBRIDIZATION
+++ = STRONG HYBRIDIZATION
++ = WEAK BUT READILY DETECTABLE
+ = VERY WEAK
+/− = BARELY DETECTABLE
− = ZERO
ND = NOT DETERMINED
\* = UNDILUTED CULTURE
\*\* = CULTURE DILUTED 1:20

SOURCE KEY:
(1) CENTER FOR DISEASE CONTROL, ATLANTA, GA.
(2) CENTER FOR LABORATORIES, STATE LABORATORIES INSTITUTE
(3) UNIVERSITY OF MASSACHUSETTS MEDICAL CENTER, WORCHESTER, MA
(4) CENTRAL PUBLIC HEALTH, COLLEGIATE AVE, LONDON ENGLAND
(5) SILLIKER LABORATORIES, CHICAGO, IL
(6) AMERICAN TYPE CULTURE COLLECTION, BETHESDA, MD.

TABLE 3

HYBRIDIZATION OF SALMONELLA PROBES TO REPRESENTATIVE NON-SALMONELLA BACTERIA

| GENUS | SPECIES | STRAIN | SOURCE | DOT BLOT HYBRIDIZATION 849 | 1165 | 1200 | 1166 | LIQUID HYBRIDIZATION 1200 1166 | 1165 1200 1166 | 849 1166 | 849 1200 1166 1069 |
|---|---|---|---|---|---|---|---|---|---|---|---|
| Alteromonas | putrefaciens | ATCC8071 | (6) | − | − | − | − | ND | ND | ND | ND |
| Aeromonas | sobria | ATCC9091 | (6) | ND | ND | ND | ND | ND | 0.00 | ND | 0.00 |
| Citrobacter | amalonaticus | 9020-77 | (8) | − | − | − | ++++ | 0.02 | 0.00 | 0.00 | 0.00 |
| Citrobacter | amalonaticus | ATCC25405 | (6) | − | − | − | +++ | 0.01 | 0.00 | 0.00 | 0.00 |
| Citrobacter | amalonaticus | ATCC25406 | (6) | − | − | − | ++++ | 0.00 | 0.00 | 0.00 | 0.00 |
| Citrobacter | diversus | ATCC27156 | (6) | − | +/− | − | +++ | ND | 0.00 | 0.02 | 0.00 |
| Citrobacter | diversus | S122B | (5) | − | − | − | − | ND | 0.00 | 0.00 | 0.00 |
| Citrobacter | diversus | 3613-63 | (8) | − | − | − | +++ | 0.02 | 0.00 | 0.00 | 0.00 |
| Citrobacter | freundii | S103B | (5) | − | − | − | − | ND | ND | ND | ND |
| Citrobacter | freundii | S135 | (5) | − | − | − | + | 0.00 | 0.00 | 0.00 | 0.00 |
| Citrobacter | freundii | 621-64 | (8) | − | − | − | ND | ND | ND | ND | ND |
| Citrobacter | freundii | 460-01 | (8) | − | − | − | − | ND | ND | ND | ND |
| Citrobacter | freundii | 6440-59 | (1) | − | − | − | − | ND | 0.00 | 0.00 | 0.00 |
| Citrobacter | freundii | ATCC29935 | (6) | − | − | − | − | ND | 0.00 | 0.00 | 0.00 |
| Citrobacter | freundii | MGH102886 | (9) | ND | ND | ND | ND | ND | 0.00 | ND | 0.00 |
| Citrobacter | freundii | 3062-62 | (1) | − | − | − | − | ND | 0.00 | ND | 0.00 |
| Citrobacter | freundii | 2970-59 | (1) | − | − | − | − | ND | 0.00 | 0.00 | 0.00 |
| Citrobacter | freundii | 892-61 | (1) | − | − | − | + | 0.00 | 0.00 | 0.00 | 0.00 |
| Citrobacter | freundii | S118A | (5) | − | − | − | − | ND | 0.00 | 0.00 | 0.00 |
| Citrobacter | freundii | 1636-61 | (1) | − | − | − | ++++ | 0.04 | 0.00 | 0.00 | 0.00 |
| Citrobacter | freundii | 3104-61 | (1) | − | − | − | ++++ | 0.00 | 0.00 | 0.00 | 0.00 |
| Citrobacter | freundii | 1637-71 | (1) | − | − | − | ++++ | 0.04 | 0.00 | 0.00 | 0.00 |
| Citrobacter | freundii | 3158-63 | (1) | − | − | − | − | ND | 0.00 | 0.00 | 0.00 |
| Citrobacter | freundii | ATCC8090 | (6) | − | − | − | − | ND | 0.00 | 0.00 | 0.00 |
| Citrobacter | freundii | ATCC33128 | (6) | − | − | − | − | ND | 0.00 | 0.00 | 0.00 |
| Citrobacter | freundii | 2990-58 | (1) | − | − | − | − | ND | 0.00 | 0.00 | 0.00 |
| Citrobacter | sp. | IG3237 | (8) | − | − | − | − | ND | ND | ND | ND |
| Citrobacter | sp. | IG3241 | (8) | − | − | − | ++++ | 0.09 | 0.00 | 0.00 | 0.00 |
| Citrobacter | sp. | IG3238 | (8) | − | − | − | − | 0.00 | 0.00 | 0.00 | 0.00 |
| Citrobacter | sp. | IG3240 | (8) | − | − | − | − | ND | 0.00 | ND | 0.00 |
| Citrobacter | sp. | IG3239 | (8) | − | − | − | ++++ | ND | 0.00 | ND | 0.00 |
| Enterobacter | aerogenes | ATCC13048 | (6) | − | − | − | − | ND | 0.00 | 0.00 | 0.00 |
| Enterobacter | aerogenes | S123A | (5) | − | − | − | − | ND | 0.00 | 0.00 | 0.00 |
| Enterobacter | aerogenes | ATCC29940 | (6) | − | − | − | − | 0.00 | 0.00 | 0.00 | 0.00 |
| Enterobacter | agglomerans | ATCC29915 | (6) | − | − | − | ++++ | ND | 0.00 | 0.00 | 0.00 |
| Enterobacter | agglomerans | ATCC29917 | (6) | − | − | − | + | ND | 0.00 | 0.00 | 0.00 |
| Enterobacter | agglomerans | ATCC29921 | (6) | − | − | − | + | 0.00 | 0.00 | 0.00 | 0.00 |
| Enterobacter | agglomerans | ATCC27998 | (6) | − | − | − | +++ | 0.00 | 0.00 | 0.00 | 0.00 |
| Enterobacter | agglomerans | S121B | (5) | − | − | − | ++++ | ND | 0.00 | 0.00 | 0.00 |
| Enterobacter | agglomerans | ATCC29916 | (6) | − | − | − | + | ND | 0.00 | 0.00 | 0.00 |
| Enterobacter | agglomerans | ATCC29919 | (6) | − | − | − | + | 0.00 | 0.00 | 0.00 | 0.00 |
| Enterobacter | agglomerans | GT0049 | (7) | − | − | − | ++++ | 0.00 | 0.00 | 0.00 | 0.00 |
| Enterobacter | agglomerans | ATCC29923 | (6) | − | − | − | + | 0.01 | 0.00 | 0.00 | 0.01 |
| Enterobacter | agglomerans | ATCC29918 | (6) | − | − | − | ++++ | 0.00 | 0.00 | 0.00 | 0.02 |
| Enterobacter | agglomerans | ATCC29904 | (6) | − | − | − | ++++ | ND | 0.00 | 0.00 | 0.00 |
| Enterobacter | agglomerans | ATCC29920 | (6) | − | − | − | + | 0.00 | 0.00 | 0.00 | 0.00 |

TABLE 3-continued
HYBRIDIZATION OF SALMONELLA PROBES TO REPRESENTATIVE NON-SALMONELLA BACTERIA

| | | | | DOT BLOT HYBRIDIZATION | | | | LIQUID HYBRIDIZATION | | | |
|---|---|---|---|---|---|---|---|---|---|---|---|
| GENUS | SPECIES | STRAIN | SOURCE | 849 | 1165 | 1200 | 1166 | 1200 1166 | 1165 1200 1166 | 849 1166 | 849 1200 1166 1069 |
| Enterobacter | agglomerans | ATCC29922 | (6) | − | − | − | ++++ | ND | 0.00 | 0.00 | 0.00 |
| Enterobacter | amnigenus | ATCC33072 | (6) | − | − | − | ++ | ND | 0.00 | 0.00 | 0.00 |
| Enterobacter | sp. CDC grp. 19 | GT1610 | (7) | − | − | − | − | ND | ND | ND | ND |
| Enterobacter | cloacae | GT0059 | (7) | − | − | − | ND | ND | 0.00 | 0.01 | 0.00 |
| Enterobacter | cloacae | S134 | (5) | − | − | − | − | ND | 0.00 | 0.00 | 0.00 |
| Enterobacter | cloacae | S121A | (5) | − | − | − | − | ND | 0.00 | 0.00 | 0.00 |
| Enterobacter | cloacae | 126lac+ | (7) | − | − | − | − | ND | ND | ND | ND |
| Enterobacter | cloacae | S121F | (5) | ND | ND | ND | ND | ND | 0.00 | ND | 0.00 |
| Enterobacter | cloacae | GT0060 | (7) | ND | ND | ND | ND | ND | 0.00 | ND | 0.00 |
| Enterobacter | cloacae | IG3068 | (7) | ND | ND | ND | ND | ND | 0.00 | ND | 0.00 |
| Enterobacter | cloacae | GT0058 | (7) | ND | ND | ND | ND | ND | 0.00 | ND | 0.00 |
| Enterobacter | cloacae | ATCC13047 | (6) | − | − | − | ++ | ND | 0.00 | 0.00 | 0.00 |
| Enterobacter | cloacae | S103B | (5) | ND | ND | ND | ND | 0.04 | 0.00 | 0.00 | 0.00 |
| Enterobacter | cloacae | GT0055 | (7) | ND | ND | ND | ND | 0.02 | 0.00 | 0.00 | 0.00 |
| Enterobacter | cloacae | GT0057 | (7) | ND | ND | ND | ND | ND | 0.00 | ND | 0.00 |
| Enterobacter | cloacae | ATCC29941 | (6) | − | − | − | − | ND | 0.00 | 0.00 | 0.00 |
| Enterobacter | cloacae | IG3102 | (7) | ND | ND | ND | ND | ND | 0.00 | ND | 0.00 |
| Enterobacter | cloacae | IG3068 | (7) | − | − | − | ++++ | 0.01 | 0.00 | 0.00 | 0.00 |
| Enterobacter | cloacae | GT0056 | (7) | ND | ND | ND | ND | ND | 0.00 | ND | 0.00 |
| Enterobacter | cloacae | GT0054 | (7) | ND | ND | ND | ND | ND | 0.00 | ND | 0.00 |
| Enterobacter | gergoviae | ATCC33028 | (6) | − | − | − | +++ | ND | 0.00 | 0.01 | 0.00 |
| Enterobacter | intermedium | ATCC33110 | (6) | − | − | − | ++ | ND | 0.00 | 0.00 | 0.00 |
| Enterobacter | sakazakii | GT0063 | (7) | − | − | − | ++++ | ND | 0.00 | 0.00 | 0.00 |
| Enterobacter | sakazakii | GT0062 | (7) | ND | ND | ND | ND | ND | 0.00 | ND | 0.00 |
| Enterobacter | sakazakii | ATCC29544 | (6) | − | − | − | ++++ | ND | 0.00 | 0.00 | 0.00 |
| Enterobacter | sakazakii | GT0064 | (7) | ND | ND | ND | ND | ND | 0.00 | ND | 0.00 |
| Enterobacter | taylorae | ATCC35317 | (6) | − | − | − | − | ND | 0.00 | 0.00 | 0.00 |
| Enterobacter | taylorae | GT0065 | (7) | ND | ND | ND | ND | ND | 0.00 | ND | 0.00 |
| Escherichia | coli | IG977 | (7) | − | − | − | ND | ND | ND | ND | ND |
| Escherichia | coli | IG781 | (3) | ND | ND | ND | ND | 0.00 | 0.00 | 0.00 | 0.00 |
| Escherichia | coli | IG3066 | (7) | − | − | − | ++++ | 0.01 | 0.00 | 0.00 | 0.00 |
| Escherichia | coli | IG3097 | (7) | − | − | − | +++ | 0.02 | 0.00 | 0.00 | 0.00 |
| Escherichia | coli | IG3076 | (7) | − | − | − | ++++ | 0.12 | 0.00 | 0.00 | 0.02 |
| Escherichia | coli | IG978 | (7) | − | − | − | ND | 0.01 | 0.00 | 0.00 | 0.01 |
| Escherichia | coli | GT0796 | (7) | − | − | − | + | 0.00 | 0.00 | 0.00 | 0.00 |
| Escherichia | coli | IG3064 | (7) | − | − | − | ++++ | 0.00 | 0.00 | 0.00 | 0.00 |
| Hafnia | alvei | ATCC29927 | (6) | − | − | − | ++ | 0.00 | 0.00 | 0.00 | 0.00 |
| Hafnia | alvei | IG3107 | (7) | − | − | − | + | 0.01 | 0.00 | 0.00 | 0.00 |
| Klebsiella | oxytoca | RF501B | (7) | − | − | − | − | ND | 0.00 | 0.03 | ND |
| Klebsiella | oxytoca | S121E | (5) | ND | ND | ND | ND | ND | 0.00 | ND | 0.00 |
| Klebsiella | oxytoca | IG3264 | (7) | − | − | − | + | ND | ND | ND | ND |
| Klebsiella | oxytoca | ATCC13182 | (6) | − | − | − | +/− | ND | 0.00 | 0.00 | 0.00 |
| Klebsiella | oxytoca | GT0249 | (7) | ND | ND | ND | ND | ND | 0.00 | ND | 0.00 |
| Klebsiella | oxytoca | IG3265 | (7) | − | − | − | + | ND | 0.00 | 0.00 | 0.00 |
| Klebsiella | "oxytoca" | S121C | (5) | − | − | − | − | ND | 0.00 | ND | 0.00 |
| Klebsiella | ozaenae | ATCC11296 | (6) | − | − | − | − | ND | 0.00 | 0.00 | 0.00 |
| Klebsiella | planticola | ATCC33531 | (6) | − | − | − | − | ND | 0.00 | 0.00 | 0.00 |
| Klebsiella | pneumoniae | 691t.pnk. | (7) | − | − | − | ND | ND | ND | ND | ND |
| Klebsiella | pneumoniae | 72mauve | (7) | − | − | − | ND | ND | ND | ND | ND |
| Klebsiella | pneumoniae | ATCC29939 | (6) | − | − | − | − | ND | 0.00 | 0.00 | 0.00 |
| Klebsiella | pneumoniae | ATCC13883 | (6) | − | − | − | − | ND | 0.00 | 0.00 | 0.00 |
| Klebsiella | pneumoniae | GT0251 | (7) | ND | ND | ND | ND | ND | 0.00 | ND | 0.00 |
| Klebsiella | pneumoniae | IG3082 | (7) | ND | ND | ND | ND | 0.00 | 0.00 | 0.00 | 0.00 |
| Klebsiella | pneumoniae | IG3058 | (7) | ND | ND | ND | ND | ND | 0.00 | ND | 0.00 |
| Klebsiella | pneumoniae | GT0254 | (7) | ND | ND | ND | ND | ND | 0.00 | ND | 0.00 |
| Klebsiella | pneumoniae | IG3088 | (7) | − | − | − | − | 0.03 | 0.00 | 0.00 | 0.00 |
| Klebsiella | terrigena | ATCC33257 | (6) | − | − | − | ++++ | ND | 0.00 | 0.00 | 0.00 |
| Morganella | morganii | IG3108 | (7) | ND | ND | ND | ND | ND | 0.00 | ND | 0.00 |
| Morganella | morganii | IG3063 | (7) | − | − | − | − | 0.02 | 0.00 | 0.00 | 0.00 |
| Proteus | mirabilis | ATCC29906 | (6) | − | − | − | − | ND | 0.00 | 0.00 | 0.00 |
| Proteus | mirabilis | ATCC25933 | (6) | − | − | − | − | ND | 0.00 | 0.00 | 0.00 |
| Proteus | mirabilis | ATCC7002 | (6) | − | − | − | − | ND | 0.00 | 0.00 | 0.00 |
| Proteus | mirabilis | IG3098 | (7) | − | − | − | − | 0.00 | 0.00 | 0.00 | 0.00 |
| Proteus | mirabilis | IG3109 | (7) | − | +/− | − | − | 0.01 | 0.00 | 0.00 | 0.01 |
| Proteus | rettgeri | ATCC29944 | (6) | ND | ND | ND | ND | ND | 0.00 | ND | 0.00 |
| Proteus | vulgaris | S118B | (5) | − | − | − | − | ND | 0.00 | 0.00 | 0.00 |
| Proteus | vulgaris | S133 | (5) | − | − | − | − | ND | 0.00 | 0.00 | 0.00 |
| Providencia | alcalifaciens | ATCC9886 | (6) | ND | ND | ND | ND | ND | 0.00 | ND | 0.00 |
| Providencia | alcalifaciens | ATCC27970 | (6) | ND | ND | ND | ND | ND | 0.00 | ND | 0.00 |
| Providencia | rustigiani | ATCC33673 | (6) | ND | ND | ND | ND | ND | 0.00 | ND | 0.00 |
| Providencia | stuartii | ATCC29914 | (6) | ND | ND | ND | ND | ND | 0.00 | ND | 0.00 |
| Serratia | marcescens | ATCC29937 | (6) | − | − | − | ++++ | ND | 0.00 | 0.04 | 0.00 |
| Serratia | marcescens | IG3095 | (7) | − | +/− | − | +++ | 0.00 | 0.00 | 0.00 | 0.01 |
| Serratia | odorifera | 83mauve | (7) | − | − | − | − | ND | ND | ND | ND |

TABLE 3-continued

HYBRIDIZATION OF SALMONELLA PROBES TO REPRESENTATIVE NON-SALMONELLA BACTERIA

| GENUS | SPECIES | STRAIN | SOURCE | DOT BLOT HYBRIDIZATION | | | | LIQUID HYBRIDIZATION | | | |
|---|---|---|---|---|---|---|---|---|---|---|---|
| | | | | 849 | 1165 | 1200 | 1166 | 1200 1166 | 1165 1200 1166 | 849 1166 | 849 1200 1166 1069 |
| Shigella | boydii | ATCC29929 | (6) | — | — | — | ++++ | 0.03 | 0.00 | 0.00 | 0.00 |
| Shigella | boydii | ATCC8700 | (6) | — | — | — | ++++ | 0.00 | 0.00 | 0.00 | 0.00 |
| Shigella | boydii | ATCC29928 | (6) | — | — | — | ++++ | 0.01 | 0.00 | 0.00 | 0.00 |
| Shigella | dysentariae | ATCC13313 | (6) | — | — | — | ++++ | ND | 0.00 | 0.00 | 0.00 |
| Shigella | flexneri | ATCC29903 | (6) | — | — | — | ++++ | ND | 0.00 | 0.00 | 0.00 |
| Shigella | sonnei | ATCC29930 | (6) | — | — | — | ++ | 0.01 | 0.00 | 0.00 | 0.00 |
| Yersinia | enterocolitica | RF954 | (7) | — | — | — | ++++ | 0.00 | 0.00 | 0.00 | 0.00 |
| Yersinia | enterocolitica | GT0424 | (7) | — | — | — | ++++ | ND | 0.00 | 0.00 | 0.00 |
| Yersinia | enterocolitica | RF955 | (7) | — | — | — | ND | ND | ND | ND | ND |
| Salmonella | typhimurium | ATCC23566 | (6) | ++++ | ++++ | ++++ | ++++ | 1.07 | 2.00 | ND | ND |
| NO BACTERIA | (GN BROTH) | CONTROL | | ND | ND | ND | ND | 0.00 | 0.00 | 0.00 | 0.00 |

REACTION KEY:
++++ = POSITIVE CONTROL LEVEL OF HYBRIDIZATION
+++ = STRONG HYBRIDIZATION
++ = WEAK BUT READILY DETECTABLE
+ = VERY WEAK
+/- = BARELY DETECTABLE
- = NO DETECTABLE HYBRIDIZATION
ND = NOT DETERMINED
SOURCE KEY:
(1) CENTERS FOR DISEASE CONTROL, ATLANTA, GA.
(3) GARY DOERN, UNIV. MASSACHUSETTS, AMHERST, MA.
(5) SILLIKER LABORATORIES, CHICAGO, IL.
(6) AMERICAN TYPE CULTURE COLLECTION, BETHESDA, MD.
(7) GENE-TRAK SYSTEMS/INTEGRATED GENETICS, FRAMINGHAM, MA.
(8) GEORGE FANNING, WALTER REED ARMY HOSPITAL, WASHINGTON, D.C.
(9) MASSACHUSETTS GENERAL HOSPITAL, BOSTON, MA.

TABLE 4

USE OF PROBES TO DETECT SALMONELLA IN FOOD SAMPLES.

| SAMPLE NO. | FOOD TYPE | SALMONELLA SPECIES | STRAIN | CFU PER SAMPLE | ASSAY O.D. 450 NM | BAM RESULT |
|---|---|---|---|---|---|---|
| 1 | GROUND PORK | ANATUM | 765 | 94 | 2.01 | + |
| 2 | GROUND PORK | ANATUM | 765 | 94 | 2.00 | + |
| 3 | GROUND PORK | ANATUM | 765 | 9 | 2.01 | + |
| 4 | GROUND PORK | ANATUM | 765 | 9 | 1.99 | + |
| 5 | GROUND PORK | CONTROL | — | 0 | 0.01 | — |
| 6 | GROUND PORK | ANATUM | 765 | 94 | 1.99 | + |
| 7 | GROUND PORK | ANATUM | 765 | 94 | 2.01 | + |
| 8 | GROUND PORK | ANATUM | 765 | 9 | 1.94 | + |
| 9 | GROUND PORK | ANATUM | 765 | 9 | 1.93 | + |
| 10 | GROUND PORK | CONTROL | — | 0 | 0.00 | — |
| 11 | ROAST BEEF | AGONA | 611 | 118 | 1.98 | + |
| 12 | ROAST BEEF | AGONA | 611 | 118 | 1.97 | + |
| 13 | ROAST BEEF | AGONA | 611 | 12 | 2.01 | + |
| 14 | ROAST BEEF | AGONA | 611 | 12 | 1.92 | + |
| 15 | ROAST BEEF | CONTROL | — | 0 | 0.02 | — |
| 16 | ROAST BEEF | AGONA | 611 | 118 | 1.97 | + |
| 17 | ROAST BEEF | AGONA | 611 | 118 | 1.98 | + |
| 18 | ROAST BEEF | AGONA | 611 | 12 | 2.00 | + |
| 19 | ROAST BEEF | AGONA | 611 | 12 | 2.02 | + |
| 20 | ROAST BEEF | CONTROL | — | 0 | 0.01 | — |
| 21 | GROUND TURKEY | WELTERVREDEN | GT0911 | 77 | 2.00 | + |
| 22 | GROUND TURKEY | WELTERVREDEN | GT0911 | 77 | 0.68 | + |
| 23 | GROUND TURKEY | WELTERVREDEN | GT0911 | 8 | 1.95 | + |
| 24 | GROUND TURKEY | WELTERVREDEN | GT0911 | 8 | 1.97 | + |
| 25 | GROUND TURKEY | CONTROL | — | 0 | 0.03 | — |
| 26 | GROUND TURKEY | WELTERVREDEN | GT0911 | 77 | 1.97 | + |
| 27 | GROUND TURKEY | WELTERVREDEN | GT0911 | 77 | 1.94 | + |
| 28 | GROUND TURKEY | WELTERVREDEN | GT0911 | 8 | 1.94 | + |
| 29 | GROUND TURKEY | WELTERVREDEN | GT0911 | 8 | 1.82 | + |
| 30 | GROUND TURKEY | CONTROL | — | 0 | 0.00 | — |
| 31 | FROZEN SHRIMP | MUENSTER | 772 | 26 | 1.83 | + |
| 32 | FROZEN SHRIMP | MUENSTER | 772 | 26 | 1.96 | + |
| 33 | FROZEN SHRIMP | MUENSTER | 772 | 3 | 1.97 | + |
| 34 | FROZEN SHRIMP | MUENSTER | 772 | 3 | 1.99 | + |
| 35 | FROZEN SHRIMP | CONTROL | — | 0 | 0.00 | — |
| 36 | FROZEN SHRIMP | MUENSTER | 772 | 26 | 1.95 | + |
| 37 | FROZEN SHRIMP | MUENSTER | 772 | 26 | 1.95 | + |
| 38 | FROZEN SHRIMP | MUENSTER | 772 | 3 | 0.20 | + |
| 39 | FROZEN SHRIMP | MUENSTER | 772 | 3 | 1.97 | + |
| 40 | FROZEN SHRIMP | CONTROL | — | 0 | 0.00 | — |

TABLE 4-continued
USE OF PROBES TO DETECT SALMONELLA IN FOOD SAMPLES.

| SAMPLE NO. | FOOD TYPE | SALMONELLA SPECIES | STRAIN | CFU PER SAMPLE | ASSAY O.D. 450 NM | BAM RESULT |
|---|---|---|---|---|---|---|
| 41 | FISH | DERBY | 620 | 63 | 1.87 | + |
| 42 | FISH | DERBY | 620 | 63 | 1.57 | + |
| 43 | FISH | DERBY | 620 | 6 | 0.51 | + |
| 44 | FISH | DERBY | 620 | 6 | 0.96 | + |
| 45 | FISH | CONTROL | — | 0 | 0.00 | — |
| 46 | FISH | DERBY | 620 | 63 | 1.96 | + |
| 47 | FISH | DERBY | 620 | 63 | 1.33 | + |
| 48 | FISH | DERBY | 620 | 6 | 0.55 | + |
| 49 | FISH | DERBY | 620 | 6 | 1.30 | + |
| 50 | FISH | CONTROL | — | 0 | 0.00 | — |
| 51 | BONEMEAL | MBANDAKA | 788 | 84 | 1.95 | + |
| 52 | BONEMEAL | MBANDAKA | 788 | 84 | 1.96 | + |
| 53 | BONEMEAL | MBANDAKA | 788 | 8 | 1.95 | + |
| 54 | BONEMEAL | MBANDAKA | 788 | 8 | 1.98 | + |
| 55 | BONEMEAL | CONTROL | — | 0 | 1.93 | + |
| 56 | BONEMEAL | MBANDAKA | 788 | 84 | 1.90 | + |
| 57 | BONEMEAL | MBANDAKA | 788 | 84 | 1.87 | + |
| 58 | BONEMEAL | MBANDAKA | 788 | 8 | 1.93 | + |
| 59 | BONEMEAL | MBANDAKA | 788 | 8 | 1.95 | + |
| 60 | BONEMEAL | CONTROL | — | 0 | 1.89 | + |
| 61 | BLACK PEPPER | RUBISLAW | 792 | 73 | 1.89 | + |
| 62 | BLACK PEPPER | RUBISLAW | 792 | 73 | 1.89 | + |
| 63 | BLACK PEPPER | RUBISLAW | 792 | 7 | 1.82 | + |
| 64 | BLACK PEPPER | RUBISLAW | 792 | 7 | 1.81 | + |
| 65 | BLACK PEPPER | CONTROL | — | 0 | 0.00 | — |
| 66 | BLACK PEPPER | RUBISLAW | 792 | 73 | 1.73 | + |
| 67 | BLACK PEPPER | RUBISLAW | 792 | 73 | 1.89 | + |
| 68 | BLACK PEPPER | RUBISLAW | 792 | 7 | 1.75 | + |
| 69 | BLACK PEPPER | RUBISLAW | 792 | 7 | 1.86 | + |
| 70 | BLACK PEPPER | CONTROL | — | 0 | 0.00 | — |
| 71 | GELATIN | DERBY | 620 | 36 | 0.59 | + |
| 72 | GELATIN | DERBY | 620 | 36 | 1.70 | + |
| 73 | GELATIN | DERBY | 620 | 4 | 1.66 | + |
| 74 | GELATIN | DERBY | 620 | 4 | 1.70 | + |
| 75 | GELATIN | CONTROL | — | 0 | 0.00 | — |
| 76 | GELATIN | DERBY | 620 | 36 | 0.73 | + |
| 77 | GELATIN | DERBY | 620 | 36 | 1.88 | + |
| 78 | GELATIN | DERBY | 620 | 4 | 1.93 | + |
| 79 | GELATIN | DERBY | 620 | 4 | 1.60 | + |
| 80 | GELATIN | CONTROL | — | 0 | 0.00 | — |
| 81 | YEAST | NEW BRUNSWICK | 782 | 12 | 1.91 | + |
| 82 | YEAST | NEW BRUNSWICK | 782 | 12 | 1.93 | + |
| 83 | YEAST | NEW BRUNSWICK | 782 | 1 | 1.96 | + |
| 84 | YEAST | NEW BRUNSWICK | 782 | 1 | 1.94 | + |
| 85 | YEAST | CONTROL | — | 0 | 0.00 | — |
| 86 | YEAST | NEW BRUNSWICK | 782 | 12 | 1.58 | + |
| 87 | YEAST | NEW BRUNSWICK | 782 | 12 | 1.96 | + |
| 88 | YEAST | NEW BRUNSWICK | 782 | 1 | 1.96 | + |
| 89 | YEAST | NEW BRUNSWICK | 782 | 1 | 0.00 | — |
| 90 | YEAST | CONTROL | — | 0 | 0.00 | — |
| 91 | SOY FLOUR | CERRO | 806 | 450 | 1.88 | + |
| 92 | SOY FLOUR | CERRO | 806 | 450 | 1.89 | + |
| 93 | SOY FLOUR | CERRO | 806 | 45 | 1.87 | + |
| 94 | SOY FLOUR | CERRO | 806 | 45 | 1.82 | + |
| 95 | SOY FLOUR | CONTROL | — | 0 | 0.00 | — |
| 96 | SOY FLOUR | CERRO | 806 | 450 | 1.78 | + |
| 97 | SOY FLOUR | CERRO | 806 | 450 | 1.93 | + |
| 98 | SOY FLOUR | CERRO | 806 | 45 | 1.90 | + |
| 99 | SOY FLOUR | CERRO | 806 | 45 | 1.85 | + |
| 100 | SOY FLOUR | CONTROL | — | 0 | 0.00 | — |
| 101 | ELBOW MACARONI | DRYPOOL | GT0621 | 22 | 1.73 | + |
| 102 | ELBOW MACARONI | DRYPOOL | GT0621 | 22 | 1.93 | + |
| 103 | ELBOW MACARONI | DRYPOOL | GT0621 | 2 | 1.89 | + |
| 104 | ELBOW MACARONI | DRYPOOL | GT0621 | 2 | 1.92 | + |
| 105 | ELBOW MACARONI | CONTROL | — | 0 | 0.05 | — |
| 106 | ELBOW MACARONI | DRYPOOL | GT0621 | 22 | 1.82 | + |
| 107 | ELBOW MACARONI | DRYPOOL | GT0621 | 22 | 1.99 | + |
| 108 | ELBOW MACARONI | DRYPOOL | GT0621 | 2 | 1.96 | + |
| 109 | ELBOW MACARONI | DRYPOOL | GT0621 | 2 | 1.98 | + |
| 110 | ELBOW MACARONI | CONTROL | — | 0 | 0.00 | — |
| 111 | CHEESE POWDER | MELEAGRIDIS | 771 | 19 | 1.86 | + |
| 112 | CHEESE POWDER | MELEAGRIDIS | 771 | 19 | 1.90 | + |
| 113 | CHEESE POWDER | MELEAGRIDIS | 771 | 2 | 1.88 | + |
| 114 | CHEESE POWDER | MELEAGRIDIS | 771 | 2 | 1.86 | + |
| 115 | CHEESE POWDER | CONTROL | — | 0 | 0.00 | — |
| 116 | CHEESE POWDER | MELEAGRIDIS | 771 | 19 | 1.54 | + |
| 117 | CHEESE POWDER | MELEAGRIDIS | 771 | 19 | 1.93 | + |
| 118 | CHEESE POWDER | MELEAGRIDIS | 771 | 2 | 1.93 | + |

TABLE 4-continued
USE OF PROBES TO DETECT SALMONELLA IN FOOD SAMPLES.

| SAMPLE NO. | FOOD TYPE | SALMONELLA SPECIES | STRAIN | CFU PER SAMPLE | ASSAY O.D. 450 NM | BAM RESULT |
|---|---|---|---|---|---|---|
| 119 | CHEESE POWDER | MELEAGRIDIS | 771 | 2 | 1.91 | + |
| 120 | CHEESE POWDER | CONTROL | — | 0 | 0.00 | — |
| 121 | DRY CASEIN | HAVANA | 799 | 15 | 0.12 | + |
| 122 | DRY CASEIN | HAVANA | 799 | 15 | 0.14 | + |
| 123 | DRY CASEIN | HAVANA | 799 | 2 | 0.12 | + |
| 124 | DRY CASEIN | HAVANA | 799 | 2 | 0.15 | + |
| 125 | DRY CASEIN | CONTROL | — | 0 | 0.00 | — |
| 126 | DRY CASEIN | HAVANA | 799 | 15 | 0.08 | + |
| 127 | DRY CASEIN | HAVANA | 799 | 15 | 0.04 | + |
| 128 | DRY CASEIN | HAVANA | 799 | 2 | 0.19 | + |
| 129 | DRY CASEIN | HAVANA | 799 | 2 | 0.21 | + |
| 130 | DRY CASEIN | CONTROL | — | 0 | 0.00 | — |
| 131 | PEANUT BUTTER | CUBANA | GT0661 | 640 | 1.97 | + |
| 132 | PEANUT BUTTER | CUBANA | GT0661 | 640 | 1.99 | + |
| 133 | PEANUT BUTTER | CUBANA | GT0661 | 64 | 2.00 | + |
| 134 | PEANUT BUTTER | CUBANA | GT0661 | 64 | 1.96 | + |
| 135 | PEANUT BUTTER | CONTROL | — | 0 | 0.00 | — |
| 136 | PEANUT BUTTER | CUBANA | GT0661 | 640 | 1.95 | + |
| 137 | PEANUT BUTTER | CUBANA | GT0661 | 640 | 1.98 | + |
| 138 | PEANUT BUTTER | CUBANA | GT0661 | 64 | 1.97 | + |
| 139 | PEANUT BUTTER | CUBANA | GT0661 | 64 | 1.96 | + |
| 140 | PEANUT BUTTER | CONTROL | — | 0 | 0.00 | — |
| 141 | COCONUT | RUBISLAW | 792 | 840 | 1.95 | + |
| 142 | COCONUT | RUBISLAW | 792 | 840 | 1.98 | + |
| 143 | COCONUT | RUBISLAW | 792 | 84 | 1.93 | + |
| 144 | COCONUT | RUBISLAW | 792 | 84 | 1.96 | + |
| 145 | COCONUT | CONTROL | — | 0 | 0.00 | — |
| 146 | COCONUT | RUBISLAW | 792 | 840 | 1.95 | + |
| 147 | COCONUT | RUBISLAW | 792 | 840 | 1.94 | + |
| 148 | COCONUT | RUBISLAW | 792 | 84 | 1.95 | + |
| 149 | COCONUT | RUBISLAW | 792 | 84 | 2.00 | + |
| 150 | COCONUT | CONTROL | — | 0 | 0.00 | — |
| 151 | PECANS | TYPHIMURIUM | 654 | 690 | 1.97 | + |
| 152 | PECANS | TYPHIMURIUM | 654 | 690 | 2.04 | + |
| 153 | PECANS | TYPHIMURIUM | 654 | 69 | 1.97 | + |
| 154 | PECANS | TYPHIMURIUM | 654 | 69 | 1.97 | + |
| 155 | PECANS | CONTROL | — | 0 | 0.00 | — |
| 156 | PECANS | TYPHIMURIUM | 654 | 690 | 1.95 | + |
| 157 | PECANS | TYPHIMURIUM | 654 | 690 | 1.97 | + |
| 158 | PECANS | TYPHIMURIUM | 654 | 69 | 1.95 | + |
| 159 | PECANS | TYPHIMURIUM | 654 | 69 | 1.94 | + |
| 160 | PECANS | CONTROL | — | 0 | 0.00 | — |
| 161 | NFDM | BOVISMORBIFICANS | 704 | 940 | 1.90 | + |
| 162 | NFDM | BOVISMORBIFICANS | 704 | 940 | 1.97 | + |
| 163 | NFDM | BOVISMORBIFICANS | 704 | 94 | 1.93 | + |
| 164 | NFDM | BOVISMORBIFICANS | 704 | 94 | 1.88 | + |
| 165 | NFDM | CONTROL | — | 0 | 0.00 | — |
| 166 | NFDM | BOVISMORBIFICANS | 704 | 940 | 1.92 | + |
| 167 | NFDM | BOVISMORBIFICANS | 704 | 940 | 1.92 | + |
| 168 | NFDM | BOVISMORBIFICANS | 704 | 94 | 1.93 | + |
| 169 | NFDM | BOVISMORBIFICANS | 704 | 94 | 1.91 | + |
| 170 | NFDM | CONTROL | — | 0 | 1.83 | + |
| 171 | CHOCOLATE | SENFTENBERG | 788 | 810 | 1.90 | + |
| 172 | CHOCOLATE | SENFTENBERG | 788 | 810 | 1.81 | + |
| 173 | CHOCOLATE | SENFTENBERG | 788 | 81 | 1.83 | + |
| 174 | CHOCOLATE | SENFTENBERG | 788 | 81 | 1.84 | + |
| 175 | CHOCOLATE | CONTROL | — | 0 | 0.00 | — |
| 176 | CHOCOLATE | SENFTENBERG | 788 | 810 | 1.82 | + |
| 177 | CHOCOLATE | SENFTENBERG | 788 | 810 | 1.60 | + |
| 178 | CHOCOLATE | SENFTENBERG | 788 | 81 | 1.89 | + |
| 179 | CHOCOLATE | SENFTENBERG | 788 | 81 | 1.92 | + |
| 180 | CHOCOLATE | CONTROL | — | 0 | 0.00 | — |
| 181 | DRIED EGG | INFANTIS | 670 | 13920 | 1.91 | + |
| 182 | DRIED EGG | INFANTIS | 670 | 13920 | 1.89 | + |
| 183 | DRIED EGG | INFANTIS | 670 | 1392 | 1.93 | + |
| 184 | DRIED EGG | INFANTIS | 670 | 1392 | 1.98 | + |
| 185 | DRIED EGG | CONTROL | — | 0 | 0.00 | — |
| 186 | DRIED EGG | INFANTIS | 670 | 13920 | 1.91 | + |
| 187 | DRIED EGG | INFANTIS | 670 | 13920 | 1.88 | + |
| 188 | DRIED EGG | INFANTIS | 670 | 1392 | 1.91 | + |
| 189 | DRIED EGG | INFANTIS | 670 | 1392 | 1.91 | + |
| 190 | DRIED EGG | CONTROL | — | 0 | 0.00 | — |
| 191 | CAKE MIX | MONTEVIDEO | 678 | 820 | 1.99 | + |
| 192 | CAKE MIX | MONTEVIDEO | 678 | 820 | 1.93 | + |
| 193 | CAKE MIX | MONTEVIDEO | 678 | 82 | 1.90 | + |
| 194 | CAKE MIX | MONTEVIDEO | 678 | 82 | 1.96 | + |
| 195 | CAKE MIX | CONTROL | — | 0 | 0.00 | — |
| 196 | CAKE MIX | MONTEVIDEO | 678 | 820 | 1.94 | + |

TABLE 4-continued

USE OF PROBES TO DETECT SALMONELLA IN FOOD SAMPLES.

| SAMPLE NO. | FOOD TYPE | SALMONELLA SPECIES | STRAIN | CFU PER SAMPLE | ASSAY O.D. 450 NM | BAM RESULT |
|---|---|---|---|---|---|---|
| 197 | CAKE MIX | MONTEVIDEO | 678 | 820 | 1.96 | + |
| 198 | CAKE MIX | MONTEVIDEO | 678 | 82 | 1.90 | + |
| 199 | CAKE MIX | MONTEVIDEO | 678 | 82 | 1.95 | + |
| 200 | CAKE MIX | CONTROL | — | 0 | 0.00 | — |

CFU = COLONY-FORMING UNITS
BAM REACTION:
+ = PRESENCE OF SALMONELLA
− = ABSENCE OF SALMONELLA

What is claimed is:

1. A nucleic acid probe consisting essentially of a sequence of nucleotides of any one of probes 849, 1069, 1166, or 1200, or nucleotide sequences complementary thereto, which nucleic acid probe preferentially hybridizes to rRNA or rDNA of Salmonella over rRNA or rDNA of non-Salmonella bacteria.

2. A set of nucleic acid probes selected from the group of probe sets consisting of probes 1200 and 1165; 1200 and 1166; 1165 and 1166; 849 and 1166; 849 and 1069; 849, 1200 and 1166; 1165, 1200 and 1166; 849, 1165, 1200 and 1166; each nucleic acid probe consisting essentially of a sequence of nucleotides of any one of said probes in said sets, or nucleotide sequences complementary thereto, which nucleic acid probes preferentially hybridize to rRNA or rDNA of Salmonella over rRNA or rDNA of non-Salmonella bacteria.

3. A method for detecting the presence of Salmonella in a sample comprising:
   a) contacting said sample with at least one nucleic acid probe consisting essentially of a sequence of nucleotides of any one of probes 849, 1069, 1166, or 1200, or nucleotide sequences complementary thereto, which nucleic acid probe preferentially hybridizes to rRNA or rDNA of Salmonella over rRNA or rDNA of non-Salmonella bacteria;
   b) imposing hybridization conditions on said sample and the nucleic acid probe to allow the nucleic acid probe to hybridize to the rRNA or rDNA of Salmonella, if present in said sample to form hybridized nucleic acid complexes, under conditions which do not allow said nucleic acid probe to form stable hybridization nucleic acid complexes with non-Salmonella bacteria rRNA or rDNA; and
   c) detecting said hybridized nucleic acid complexes as an indication of the presence of said Salmonella in said sample.

4. The method of claim 3 wherein said nucleic acid probe consists essentially of any one of probes 1166, 1069, and 849 or nucleotide sequences complementary thereto.

5. A method for detecting Salmonella in a sample comprising the steps of:
   a) contacting a sample under hybridization conditions with a set of nucleic acid probes selected from the group of probe sets consisting of probes 1200 and 1165; 1200 and 1166; 1165 and 1166; 849 and 1166; 849 and 1069; 849, 1200 and 1166; 1165, 1200 and 1166; 849, 1165, 1200 and 1166; or nucleotide sequences complementary thereto, which nucleic acid probe preferentially hybridizes to rRNA or rDNA of Salmonella over rRNA or rDNA of non-Salmonella bacteria; and
   b) detecting hybridized nucleic acid complexes as an indication of the presence of Salmonella in said sample.

6. An assay kit comprising a nucleic acid probe consisting essentially of a sequence of nucleotides of any one of probes 849, 1069, 1166, or 1200, or nucleotide sequences complementary thereto, which nucleic acid probe preferentially hybridizes to rRNA or rDNA of Salmonella over rRNA or rDNA of non-Salmonella bacteria.

7. A nucleic acid probe which preferentially hybridizes to rRNA or rDNA of Salmonella over rRNA or rDNA of non-Salmonella bacteria and consists essentially of the base sequence of probe 1200, or nucleotide sequences complementary thereto.

8. A nucleic acid probe which preferentially hybridizes to rRNA or rDNA of Salmonella over rRNA or rDNA of non-Salmonella bacteria and consists essentially of the base sequence of probe 849, or nucleotide sequences complementary thereto.

* * * * *